(12) United States Patent
Von Oepen et al.

(10) Patent No.: US 8,226,603 B2
(45) Date of Patent: Jul. 24, 2012

(54) EXPANDABLE MEMBER HAVING A COVERING FORMED OF A FIBROUS MATRIX FOR INTRALUMINAL DRUG DELIVERY

(75) Inventors: Randolf Von Oepen, Los Altos Hills, CA (US); John Stankus, Campbell, CA (US); Barbara Stamberg, San Jose, CA (US); Travis R. Yribarren, San Mateo, CA (US); Richard R. Newhauser, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/237,998

(22) Filed: Sep. 25, 2008

(65) Prior Publication Data

US 2010/0076401 A1    Mar. 25, 2010

(51) Int. Cl.
*A61M 31/00* (2006.01)
*A61M 37/00* (2006.01)

(52) U.S. Cl. ......... 604/103.05; 604/101.01; 604/101.02; 604/103.02; 604/103.06; 604/103.08; 604/509

(58) Field of Classification Search ............... 604/96.01, 604/103.01, 103.02, 103.05, 103.06, 103.08, 604/101.01, 101.02, 509
See application file for complete search history.

(56) References Cited

U.S. PATENT DOCUMENTS

| | | | |
|---|---|---|---|
| 4,564,014 A | 1/1986 | Fogarty et al. | |
| 4,878,906 A | 11/1989 | Lindemann et al. | |
| 4,959,074 A | 9/1990 | Halpern et al. | |
| 4,990,357 A | 2/1991 | Karakelle et al. | |
| 5,026,607 A | 6/1991 | Kiezulas | |
| 5,049,131 A | 9/1991 | Deuss | |
| 5,061,273 A | 10/1991 | Yock | |
| 5,092,841 A | 3/1992 | Spears | |
| 5,102,402 A * | 4/1992 | Dror et al. | 604/265 |
| 5,272,012 A | 12/1993 | Opolski | |
| 5,295,978 A | 3/1994 | Fan et al. | |
| 5,304,121 A | 4/1994 | Sahatjian | |
| 5,324,261 A | 6/1994 | Amundson et al. | |
| 5,370,614 A | 12/1994 | Amundson et al. | |
| 5,380,299 A | 1/1995 | Fearnot et al. | |
| 5,456,694 A | 10/1995 | Marin et al. | |
| 5,458,573 A | 10/1995 | Summers | |
| 5,458,615 A | 10/1995 | Klemm et al. | |
| 5,476,476 A | 12/1995 | Hillstead | |

(Continued)

FOREIGN PATENT DOCUMENTS

DE    10244847    4/2004

(Continued)

OTHER PUBLICATIONS

Kesting, Robert E., "Phase Inversion Membranes," in Synthetic Polymeric Membranes, 2nd Ed., Chapter 7, pp. 237-286, 1985.

(Continued)

*Primary Examiner* — Bhisma Mehta
*Assistant Examiner* — Larry R Wilson
(74) *Attorney, Agent, or Firm* — Baker Botts LLP

(57) ABSTRACT

The present invention generally relates to an intraluminal catheter device for use in angioplasty and delivery of a therapeutic agent. Particularly, the present invention is directed to a catheter having an expandable member having a therapeutic agent disposed thereon and a fibrous matrix covering for delivering a therapeutic agent and methods of using the same.

18 Claims, 13 Drawing Sheets

U.S. PATENT DOCUMENTS

| | | |
|---|---|---|
| 5,507,768 A | 4/1996 | Lau et al. |
| 5,549,551 A | 8/1996 | Peacock, III et al. |
| 5,562,922 A | 10/1996 | Lambert |
| 5,578,340 A | 11/1996 | Ogawa et al. |
| 5,588,962 A | 12/1996 | Nicholas et al. |
| 5,609,629 A | 3/1997 | Fearnot et al. |
| 5,620,738 A | 4/1997 | Fan et al. |
| 5,674,192 A | 10/1997 | Sahatjian et al. |
| 5,685,847 A | 11/1997 | Barry |
| 5,707,385 A | 1/1998 | Williams |
| 5,728,420 A | 3/1998 | Keogh |
| 5,733,925 A | 3/1998 | Kunz et al. |
| 5,756,144 A | 5/1998 | Wolff et al. |
| 5,766,158 A | 6/1998 | Opolski |
| 5,782,855 A | 7/1998 | Lau et al. |
| 5,820,917 A | 10/1998 | Tuch |
| 5,820,918 A | 10/1998 | Ronan et al. |
| 5,821,343 A | 10/1998 | Keogh |
| 5,824,049 A | 10/1998 | Ragheb et al. |
| 5,837,313 A | 11/1998 | Ding et al. |
| 5,843,033 A | 12/1998 | Ropiak |
| 5,843,089 A | 12/1998 | Sahatjian et al. |
| 5,860,954 A | 1/1999 | Ropiak |
| 5,868,719 A | 2/1999 | Tsukernik |
| 5,891,506 A | 4/1999 | Keogh |
| 5,893,840 A | 4/1999 | Hull et al. |
| 5,900,246 A | 5/1999 | Lambert |
| 5,914,182 A | 6/1999 | Drumheller |
| 5,925,552 A | 7/1999 | Keogh et al. |
| 5,928,916 A | 7/1999 | Keogh |
| 5,945,319 A | 8/1999 | Keogh |
| 5,954,706 A | 9/1999 | Sahatjian |
| 5,977,163 A | 11/1999 | Li et al. |
| 5,980,972 A | 11/1999 | Ding |
| 5,981,568 A | 11/1999 | Kunz et al. |
| 6,010,521 A | 1/2000 | Lee et al. |
| 6,017,741 A | 1/2000 | Keogh |
| 6,033,719 A | 3/2000 | Keogh |
| 6,039,721 A | 3/2000 | Johnson et al. |
| 6,048,620 A | 4/2000 | Zhong |
| 6,050,980 A | 4/2000 | Wilson |
| 6,074,659 A | 6/2000 | Kunz et al. |
| 6,093,463 A | 7/2000 | Thakrar |
| 6,096,726 A | 8/2000 | Opolski |
| 6,099,562 A | 8/2000 | Ding et al. |
| 6,099,926 A | 8/2000 | Thakrar |
| 6,106,889 A | 8/2000 | Beavers et al. |
| 6,107,416 A | 8/2000 | Patnaik et al. |
| 6,110,590 A | 8/2000 | Zarkoob et al. |
| 6,129,705 A | 10/2000 | Grantz |
| 6,143,037 A | 11/2000 | Goldstein et al. |
| 6,146,358 A | 11/2000 | Rowe |
| 6,200,257 B1 | 3/2001 | Winkler |
| 6,214,901 B1 | 4/2001 | Chudzik et al. |
| 6,218,016 B1 | 4/2001 | Tedeschi et al. |
| 6,248,127 B1 | 6/2001 | Shah et al. |
| 6,254,921 B1 | 7/2001 | Chappa et al. |
| 6,264,633 B1 * | 7/2001 | Knorig ............... 604/102.01 |
| 6,268,390 B1 | 7/2001 | Kunz |
| 6,270,831 B2 | 8/2001 | Kumar et al. |
| 6,280,411 B1 | 8/2001 | Lennox |
| 6,303,179 B1 | 10/2001 | Koulik et al. |
| 6,306,166 B1 | 10/2001 | Barry et al. |
| 6,306,421 B1 | 10/2001 | Kunz et al. |
| 6,335,029 B1 * | 1/2002 | Kamath et al. ............ 424/423 |
| 6,364,856 B1 | 4/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,379,691 B1 | 4/2002 | Tedeschi et al. |
| 6,382,526 B1 | 5/2002 | Reneker et al. |
| 6,395,208 B1 * | 5/2002 | Herweck et al. ............ 264/127 |
| 6,409,716 B1 | 6/2002 | Sahatjian et al. |
| 6,419,692 B1 | 7/2002 | Yang et al. |
| 6,443,942 B2 | 9/2002 | Van Antwerp et al. |
| 6,447,835 B1 | 9/2002 | Wang et al. |
| 6,461,666 B2 | 10/2002 | Park |
| 6,475,434 B1 | 11/2002 | Darouiche |
| 6,491,938 B2 | 12/2002 | Kunz et al. |
| 6,491,965 B1 | 12/2002 | Berry et al. |
| 6,506,408 B1 | 1/2003 | Palasis |
| 6,506,411 B2 | 1/2003 | Hunter et al. |
| 6,515,009 B1 | 2/2003 | Kunz et al. |
| 6,517,888 B1 | 2/2003 | Weber |
| 6,520,425 B1 | 2/2003 | Reneker |
| 6,521,283 B1 | 2/2003 | Yianni |
| 6,524,274 B1 | 2/2003 | Rosenthal et al. |
| 6,537,194 B1 | 3/2003 | Winkler |
| 6,544,221 B1 | 4/2003 | Kokish et al. |
| 6,544,223 B1 | 4/2003 | Kokish |
| 6,544,544 B2 | 4/2003 | Hunter et al. |
| 6,545,097 B2 | 4/2003 | Pinchuk et al. |
| 6,555,157 B1 | 4/2003 | Hossainy |
| 6,555,225 B1 | 4/2003 | Yoshioka et al. |
| 6,571,771 B2 | 6/2003 | Doering et al. |
| 6,579,539 B2 | 6/2003 | Lawson et al. |
| 6,589,546 B2 | 7/2003 | Kamath et al. |
| 6,596,699 B2 | 7/2003 | Zamora et al. |
| 6,616,650 B1 | 9/2003 | Rowe |
| 6,617,142 B2 | 9/2003 | Keogh et al. |
| 6,627,246 B2 | 9/2003 | Mehta et al. |
| 6,638,563 B2 | 10/2003 | McGee et al. |
| 6,641,611 B2 | 11/2003 | Jayaraman |
| 6,645,547 B1 | 11/2003 | Shekalim et al. |
| 6,649,030 B1 | 11/2003 | Tesar |
| 6,656,156 B2 | 12/2003 | Yang et al. |
| 6,663,881 B2 | 12/2003 | Kunz et al. |
| 6,669,980 B2 | 12/2003 | Hansen |
| 6,673,453 B2 | 1/2004 | Beavers et al. |
| 6,676,987 B2 | 1/2004 | Zhong et al. |
| 6,683,062 B2 | 1/2004 | Opolski |
| 6,695,809 B1 | 2/2004 | Lee |
| 6,695,992 B2 | 2/2004 | Reneker |
| 6,706,408 B2 | 3/2004 | Jelle |
| 6,713,119 B2 | 3/2004 | Hossainy et al. |
| 6,719,991 B2 | 4/2004 | Darouiche et al. |
| 6,730,349 B2 | 5/2004 | Schwarz et al. |
| 6,733,819 B2 | 5/2004 | Burkett et al. |
| 6,737,447 B1 | 5/2004 | Smith et al. |
| 6,743,462 B1 | 6/2004 | Pacetti |
| 6,743,463 B2 | 6/2004 | Weber et al. |
| 6,743,521 B2 | 6/2004 | Hubbell et al. |
| 6,753,071 B1 | 6/2004 | Pacetti |
| 6,753,454 B1 | 6/2004 | Smith et al. |
| 6,764,709 B2 | 7/2004 | Flanagan |
| 6,776,771 B2 | 8/2004 | van Moorlegem et al. |
| 6,793,960 B1 | 9/2004 | Michal et al. |
| 6,818,247 B1 | 11/2004 | Chen et al. |
| 6,821,479 B1 | 11/2004 | Smith et al. |
| 6,821,528 B2 | 11/2004 | Scott et al. |
| 6,828,028 B1 | 12/2004 | Fukui et al. |
| 6,830,583 B2 | 12/2004 | Shah et al. |
| 6,833,153 B1 | 12/2004 | Roorda et al. |
| 6,855,366 B2 | 2/2005 | Smith et al. |
| 6,855,770 B2 | 2/2005 | Pinchuk et al. |
| 6,861,088 B2 | 3/2005 | Weber et al. |
| 6,865,810 B2 | 3/2005 | Stinson |
| 6,884,628 B2 | 4/2005 | Hubbell et al. |
| 6,887,270 B2 | 5/2005 | Miller et al. |
| 6,887,510 B2 | 5/2005 | Villareal |
| 6,890,339 B2 | 5/2005 | Sahatjian et al. |
| 6,899,731 B2 | 5/2005 | Li et al. |
| 6,904,310 B2 | 6/2005 | Knapp et al. |
| 6,918,869 B2 | 7/2005 | Shaw et al. |
| 6,918,927 B2 | 7/2005 | Bates et al. |
| 6,919,100 B2 | 7/2005 | Narayanan |
| 6,921,811 B2 | 7/2005 | Zamora et al. |
| 6,923,996 B2 | 8/2005 | Epstein et al. |
| 6,926,919 B1 | 8/2005 | Hossainy et al. |
| 6,939,320 B2 | 9/2005 | Lennox |
| 6,953,466 B2 | 10/2005 | Palasis et al. |
| 6,954,977 B2 | 10/2005 | Maguire et al. |
| 6,991,617 B2 | 1/2006 | Hektner et al. |
| 6,994,689 B1 | 2/2006 | Zadno Azizi et al. |
| 7,008,667 B2 | 3/2006 | Chudzik et al. |
| 7,014,913 B2 | 3/2006 | Pacetti |
| 7,048,714 B2 | 5/2006 | Richter |

| | | |
|---|---|---|
| 7,048,962 B2 | 5/2006 | Shekalim et al. |
| 7,060,051 B2 | 6/2006 | Palasis |
| 7,066,904 B2 | 6/2006 | Rosenthal et al. |
| 7,083,644 B1 | 8/2006 | Moroni |
| 7,087,135 B2 | 8/2006 | Dillon |
| 7,087,263 B2 | 8/2006 | Hossainy et al. |
| 7,105,175 B2 | 9/2006 | Schwarz |
| 7,108,684 B2 | 9/2006 | Farnan |
| 7,115,299 B2 | 10/2006 | Kokish |
| 7,122,356 B2 | 10/2006 | Keogh et al. |
| RE39,438 E | 12/2006 | Shah et al. |
| 7,163,334 B2 | 1/2007 | Chase et al. |
| 7,182,779 B2 | 2/2007 | Acosta et al. |
| 7,198,855 B2 | 4/2007 | Liebmann Vinson et al. |
| 7,201,935 B1 | 4/2007 | Claude et al. |
| 7,208,190 B2 | 4/2007 | Verlee et al. |
| 7,220,491 B2 | 5/2007 | Rouns et al. |
| 7,226,612 B2 | 6/2007 | Sohier et al. |
| 7,241,455 B2 | 7/2007 | Richard |
| 7,241,478 B2 | 7/2007 | McNeish et al. |
| 7,258,891 B2 | 8/2007 | Pacetti et al. |
| 7,267,847 B2 | 9/2007 | Karamuk |
| 7,279,175 B2 | 10/2007 | Chen et al. |
| 7,326,433 B2 | 2/2008 | Stenzel |
| 7,335,391 B1 | 2/2008 | Pacetti |
| 7,345,053 B2 | 3/2008 | Garvey |
| 7,357,940 B2 | 4/2008 | Richard et al. |
| 7,364,585 B2 | 4/2008 | Weber |
| 7,364,768 B2 | 4/2008 | Rypacek et al. |
| 7,381,418 B2 | 6/2008 | Richard |
| 7,387,810 B2 | 6/2008 | Hossainy |
| 7,390,525 B2 | 6/2008 | Epstein et al. |
| 7,398,118 B2 | 7/2008 | Knapp et al. |
| 7,402,172 B2 | 7/2008 | Chin et al. |
| 7,402,329 B2 | 7/2008 | Pacetti et al. |
| 7,407,684 B2 | 8/2008 | Spencer et al. |
| 7,442,402 B2 | 10/2008 | Chudzik et al. |
| 7,445,792 B2 | 11/2008 | Toner et al. |
| 7,449,210 B2 | 11/2008 | Malik et al. |
| 7,455,875 B2 | 11/2008 | Weber et al. |
| 7,459,169 B2 | 12/2008 | Nilsson et al. |
| 7,462,165 B2 | 12/2008 | Ding et al. |
| 7,468,210 B1 | 12/2008 | Zamora |
| 7,470,469 B1 | 12/2008 | Michal et al. |
| 7,476,246 B2 | 1/2009 | Pathak |
| 7,482,034 B2 | 1/2009 | Boulais |
| 7,485,334 B2 | 2/2009 | Kerrigan |
| 2001/0026834 A1 | 10/2001 | Chappa et al. |
| 2002/0084178 A1* | 7/2002 | Dubson et al. .............. 204/157.6 |
| 2003/0064965 A1 | 4/2003 | Richter |
| 2003/0065355 A1 | 4/2003 | Weber |
| 2003/0077253 A1 | 4/2003 | Palasis |
| 2003/0100829 A1 | 5/2003 | Zhong et al. |
| 2003/0104030 A1 | 6/2003 | Igaki et al. |
| 2003/0206960 A1 | 11/2003 | Iversen et al. |
| 2003/0207019 A1 | 11/2003 | Shekalim et al. |
| 2003/0207907 A1 | 11/2003 | Iversen et al. |
| 2003/0236513 A1 | 12/2003 | Schwarz et al. |
| 2003/0236514 A1 | 12/2003 | Schwarz |
| 2004/0018296 A1 | 1/2004 | Castro et al. |
| 2004/0034337 A1 | 2/2004 | Boulais et al. |
| 2004/0043068 A1 | 3/2004 | Tedeschi et al. |
| 2004/0058084 A1 | 3/2004 | Shekalim et al. |
| 2004/0073284 A1 | 4/2004 | Bates et al. |
| 2004/0087984 A1 | 5/2004 | Kupiecki et al. |
| 2004/0098089 A1 | 5/2004 | Weber |
| 2004/0098106 A1 | 5/2004 | Williams et al. |
| 2004/0106987 A1 | 6/2004 | Palasis et al. |
| 2004/0126400 A1 | 7/2004 | Iversen et al. |
| 2004/0224003 A1 | 11/2004 | Schultz |
| 2005/0015046 A1* | 1/2005 | Weber et al. ................ 604/96.01 |
| 2005/0025802 A1 | 2/2005 | Richard et al. |
| 2005/0025808 A1 | 2/2005 | Herrmann et al. |
| 2005/0027283 A1 | 2/2005 | Richard et al. |
| 2005/0037047 A1 | 2/2005 | Song |
| 2005/0037048 A1 | 2/2005 | Song |
| 2005/0064005 A1 | 3/2005 | Dinh et al. |
| 2005/0090891 A1 | 4/2005 | Sahatjian et al. |
| 2005/0106206 A1 | 5/2005 | Herweck et al. |
| 2005/0113687 A1 | 5/2005 | Herweck et al. |
| 2005/0163954 A1 | 7/2005 | Shaw |
| 2005/0181015 A1 | 8/2005 | Zhong |
| 2005/0182361 A1 | 8/2005 | Lennox |
| 2005/0215722 A1 | 9/2005 | Pinchunk et al. |
| 2005/0220853 A1 | 10/2005 | Dao et al. |
| 2005/0241577 A1 | 11/2005 | Shekalim et al. |
| 2005/0271701 A1 | 12/2005 | Cottone et al. |
| 2005/0278021 A1 | 12/2005 | Bates et al. |
| 2006/0008606 A1 | 1/2006 | Horn et al. |
| 2006/0013853 A1 | 1/2006 | Richard |
| 2006/0013867 A1 | 1/2006 | Richard et al. |
| 2006/0020243 A1 | 1/2006 | Speck et al. |
| 2006/0020331 A1 | 1/2006 | Bates et al. |
| 2006/0030936 A1 | 2/2006 | Weber et al. |
| 2006/0034931 A1 | 2/2006 | Hansen |
| 2006/0043650 A1 | 3/2006 | Hossainy et al. |
| 2006/0051390 A1 | 3/2006 | Schwarz |
| 2006/0073265 A1 | 4/2006 | Teichman et al. |
| 2006/0079836 A1 | 4/2006 | Holman et al. |
| 2006/0083768 A1 | 4/2006 | Labrecque et al. |
| 2006/0085023 A1 | 4/2006 | Davies et al. |
| 2006/0110209 A1 | 5/2006 | Shekalim et al. |
| 2006/0122697 A1 | 6/2006 | Shanley et al. |
| 2006/0153904 A1 | 7/2006 | Smith et al. |
| 2006/0165872 A1 | 7/2006 | Chappa et al. |
| 2006/0167407 A1 | 7/2006 | Weber et al. |
| 2006/0171981 A1 | 8/2006 | Richard et al. |
| 2006/0230476 A1 | 10/2006 | Atanasoska et al. |
| 2006/0280858 A1 | 12/2006 | Kokish |
| 2007/0003599 A1 | 1/2007 | Schwarz |
| 2007/0014827 A1 | 1/2007 | Larrick et al. |
| 2007/0048351 A1 | 3/2007 | Lunn |
| 2007/0172509 A1 | 7/2007 | Nguyen et al. |
| 2007/0212386 A1 | 9/2007 | Patravale et al. |
| 2007/0212388 A1 | 9/2007 | Patravale et al. |
| 2007/0212393 A1 | 9/2007 | Patravale et al. |
| 2007/0259017 A1 | 11/2007 | Francis |
| 2007/0298069 A1 | 12/2007 | Bucay Couto et al. |
| 2008/0015500 A1 | 1/2008 | Herweck et al. |
| 2008/0015628 A1 | 1/2008 | Dubrul et al. |
| 2008/0021385 A1 | 1/2008 | Barry et al. |
| 2008/0027531 A1 | 1/2008 | Reneker et al. |
| 2008/0050415 A1 | 2/2008 | Atanasoska et al. |
| 2008/0050418 A1 | 2/2008 | Ranade et al. |
| 2008/0051871 A1 | 2/2008 | Tuch |
| 2008/0051881 A1 | 2/2008 | Feng et al. |
| 2008/0057102 A1 | 3/2008 | Roorda |
| 2008/0085294 A1 | 4/2008 | Freyman et al. |
| 2008/0113081 A1 | 5/2008 | Hossainy et al. |
| 2008/0118544 A1 | 5/2008 | Wang |
| 2008/0124372 A1 | 5/2008 | Hossainy et al. |
| 2008/0146489 A1 | 6/2008 | Pacetti et al. |
| 2008/0181927 A1 | 7/2008 | Zhao |
| 2008/0188825 A1 | 8/2008 | Atanasoska et al. |
| 2008/0188925 A1 | 8/2008 | Zhao |
| 2008/0195079 A1 | 8/2008 | Moore et al. |
| 2008/0206442 A1 | 8/2008 | Shekalim et al. |
| 2008/0234799 A1 | 9/2008 | Acosta et al. |
| 2008/0254297 A1 | 10/2008 | Edelman |
| 2008/0255508 A1 | 10/2008 | Wang |
| 2008/0255509 A1 | 10/2008 | Wang |
| 2008/0255510 A1 | 10/2008 | Wang |
| 2008/0264336 A1 | 10/2008 | Schwarz et al. |
| 2008/0274159 A1 | 11/2008 | Schultz |
| 2009/0011116 A1 | 1/2009 | Herweck et al. |
| 2009/0299450 A1* | 12/2009 | Johnson et al. .............. 623/1.11 |
| 2010/0076377 A1 | 3/2010 | Ehrenreich et al. |

FOREIGN PATENT DOCUMENTS

| | | |
|---|---|---|
| EP | 372088 | 6/1990 |
| EP | 689465 A1 | 1/1996 |
| EP | 519063 B1 | 5/1996 |
| EP | 712615 | 5/1996 |
| EP | 797988 | 10/1997 |
| EP | 803257 | 10/1997 |
| EP | 819011 | 1/1998 |
| EP | 826382 | 3/1998 |
| EP | 879595 | 11/1998 |

| | | |
|---|---|---|
| EP | 920843 | 6/1999 |
| EP | 565604 B1 | 7/1999 |
| EP | 980280 | 2/2000 |
| EP | 992252 | 4/2000 |
| EP | 1037677 A2 | 9/2000 |
| EP | 1140273 | 10/2001 |
| EP | 708671 B1 | 11/2001 |
| EP | 1159974 | 12/2001 |
| EP | 1165157 A2 | 1/2002 |
| EP | 1220694 B1 | 4/2003 |
| EP | 1330273 | 7/2003 |
| EP | 1339440 | 9/2003 |
| EP | 1341565 | 9/2003 |
| EP | 1343544 | 9/2003 |
| EP | 1383551 A2 | 1/2004 |
| EP | 1035871 B1 | 3/2004 |
| EP | 1007135 B1 | 5/2004 |
| EP | 1447098 | 8/2004 |
| EP | 1462127 | 9/2004 |
| EP | 1539266 | 6/2005 |
| EP | 1539267 | 6/2005 |
| EP | 1562669 A1 | 8/2005 |
| EP | 1575642 | 9/2005 |
| EP | 836429 B1 | 11/2005 |
| EP | 1150622 B1 | 12/2005 |
| EP | 932399 B1 | 1/2006 |
| EP | 1610856 | 1/2006 |
| EP | 1663345 A2 | 6/2006 |
| EP | 1677849 | 7/2006 |
| EP | 1683520 | 7/2006 |
| EP | 1691856 | 8/2006 |
| EP | 1695697 | 8/2006 |
| EP | 1735042 A1 | 12/2006 |
| EP | 1750782 | 2/2007 |
| EP | 1762255 | 3/2007 |
| EP | 1800702 | 6/2007 |
| EP | 1804893 | 7/2007 |
| EP | 1666070 B1 | 9/2007 |
| EP | 1832301 | 9/2007 |
| EP | 1842567 | 10/2007 |
| EP | 1857127 | 11/2007 |
| EP | 1079872 B1 | 3/2008 |
| EP | 1952789 | 8/2008 |
| WO | WO9211890 | 7/1992 |
| WO | WO9211895 | 7/1992 |
| WO | WO9211896 | 7/1992 |
| WO | WO9421308 | 9/1994 |
| WO | WO 95/03083 A1 | 2/1995 |
| WO | WO9630064 | 10/1996 |
| WO | WO9639949 | 12/1996 |
| WO | WO9733552 | 9/1997 |
| WO | WO9811828 | 3/1998 |
| WO | WO9831415 | 7/1998 |
| WO | WO9908729 | 2/1999 |
| WO | WO9916500 | 4/1999 |
| WO | WO 99/27968 A2 | 6/1999 |
| WO | WO9929353 | 6/1999 |
| WO | WO9959649 | 11/1999 |
| WO | WO0010552 | 3/2000 |
| WO | WO0021584 | 4/2000 |
| WO | WO0032238 | 6/2000 |
| WO | WO0032267 | 6/2000 |
| WO | WO 00/48645 A2 | 8/2000 |
| WO | WO0045744 | 8/2000 |
| WO | WO 01/26702 A2 | 4/2001 |
| WO | WO0222198 | 3/2002 |
| WO | WO0243786 | 6/2002 |
| WO | WO0247731 | 6/2002 |
| WO | WO 03/002267 A1 | 1/2003 |
| WO | WO03002267 | 1/2003 |
| WO | WO03008005 | 1/2003 |
| WO | WO03045523 | 6/2003 |
| WO | WO03090684 | 11/2003 |
| WO | WO03092741 | 11/2003 |
| WO | WO2004000380 | 12/2003 |
| WO | WO2004000381 | 12/2003 |
| WO | WO2004006976 | 1/2004 |
| WO | WO2004022124 | 3/2004 |
| WO | WO2004028582 | 4/2004 |
| WO | WO2004028587 | 4/2004 |
| WO | WO2004028610 | 4/2004 |
| WO | WO2004039445 | 5/2004 |
| WO | WO2004043506 | 5/2004 |
| WO | WO2004058320 | 7/2004 |
| WO | WO2004060405 | 7/2004 |
| WO | WO2004075943 | 9/2004 |
| WO | WO 2004/091714 A2 | 10/2004 |
| WO | WO2004098671 | 11/2004 |
| WO | WO2004098697 | 11/2004 |
| WO | WO2005011766 | 2/2005 |
| WO | WO2005011767 | 2/2005 |
| WO | WO2005011768 | 2/2005 |
| WO | WO2005011772 | 2/2005 |
| WO | WO2005016399 | 2/2005 |
| WO | WO2005018501 | 3/2005 |
| WO | WO2005018606 | 3/2005 |
| WO | WO2005027994 | 3/2005 |
| WO | WO2005037339 | 4/2005 |
| WO | WO2005039664 | 5/2005 |
| WO | WO2005046747 | 5/2005 |
| WO | WO2005049021 | 6/2005 |
| WO | WO2005070008 | 8/2005 |
| WO | WO2005072651 | 8/2005 |
| WO | WO 2005/089855 A1 | 9/2005 |
| WO | WO2005079335 | 9/2005 |
| WO | WO2005079339 | 9/2005 |
| WO | WO2005079754 | 9/2005 |
| WO | WO2005097066 | 10/2005 |
| WO | WO2005098955 | 10/2005 |
| WO | WO2005105171 | 11/2005 |
| WO | WO 2005105171 A1 * | 11/2005 |
| WO | WO2005115496 | 12/2005 |
| WO | WO2006014604 | 2/2006 |
| WO | WO2006014607 | 2/2006 |
| WO | WO2006020274 | 2/2006 |
| WO | WO2006020644 | 2/2006 |
| WO | WO2006026587 | 3/2006 |
| WO | WO2006029012 | 3/2006 |
| WO | WO2006042260 | 4/2006 |
| WO | WO2006044308 | 4/2006 |
| WO | WO2006083628 | 8/2006 |
| WO | WO2006102359 | 9/2006 |
| WO | WO2006107359 | 10/2006 |
| WO | WO2006108420 | 10/2006 |
| WO | WO2006116014 | 11/2006 |
| WO | WO2006128016 | 11/2006 |
| WO | WO2006133118 | 12/2006 |
| WO | WO2007008729 | 1/2007 |
| WO | WO2007024500 | 3/2007 |
| WO | WO2007030302 | 3/2007 |
| WO | WO2007030669 | 3/2007 |
| WO | WO2007047473 | 4/2007 |
| WO | WO2007047662 | 4/2007 |
| WO | WO2007120323 | 10/2007 |
| WO | WO2007120897 | 10/2007 |
| WO | WO2007127488 | 11/2007 |
| WO | WO2008070996 | 6/2008 |
| WO | WO2008087488 | 7/2008 |
| WO | WO 2008/124310 | 10/2008 |
| WO | WO2009005933 | 1/2009 |
| WO | WO 2010/027998 | 3/2010 |

OTHER PUBLICATIONS

Tepe et al., "Local Delivery of Paclitaxel to Inhibit Restenosis During Angioplasty of the Leg," N. Engl. J. Med, 358;7, pp. 689-699, Feb. 14, 2008.

Werk et al., "Inhibition of Restenosis in Femoropopliteal Arteries Paclitaxel-Coated Versus Uncoated Balloon: Femoral Paclitaxel Randomized Pilot Trial," Circulation. 2008;118:1358-1365, Sep. 8, 2008.

U.S. Appl. No. 12/238,026, filed Sep. 25, 2008, Ehrenreich et al.
U.S. Appl. No. 12/238,627, filed Sep. 26, 2008, Ehrenreich et al.
Non-Final Rejection mailed on Feb. 8, 2010 for U.S. Appl. No. 12/238,627.
Non-Final Rejection mailed on Feb. 8, 2010 for U.S. Appl. No. 12/238,026.

Response to non-Final Rejection filed May 10, 2010 for U.S. Appl. No. 12/238,026.
Final Rejection mailed Jul. 23, 2010 for U.S. Appl. No. 12/238,026.
Response to non-Final Rejection filed May 10, 2010 for U.S. Appl. No. 12/238,627.
Final Rejection mailed Jul. 23, 2010 for U.S. Appl. No. 12/238,627.
Response to Final Rejection filed Sep. 23, 2010 for U.S. Appl. No. 12/238,026.
Response to Final Rejection filed Sep. 23, 2010 for U.S. Appl. No. 12/238,627.
Request for Continued Examination (RCE) filed Oct. 25, 2010 for U.S. Appl. No. 12/238,026.
Non-Final Rejection mailed Jan. 7, 2011 for U.S. Appl. No. 12/238,026.
Request for Continued Examination (RCE) filed Oct. 25, 2010 for U.S. Appl. No. 12/238,627.
Non-Final Rejection mailed Dec. 10, 2010 for U.S. Appl. No. 12/238,627.
U.S. Appl. No. 13/069,020, filed Mar. 22, 2011.
U.S. Appl. No. 12/238,026, filed Sep. 25, 2008.
U.S. Appl. No. 12/238,627, filed Sep. 26, 2008.
International Search Report and Written Opinion for PCT/US2011/029327, dated Jun. 21, 2011.

* cited by examiner

A-A

EXPANDABLE MEMBER HAVING A COVERING FORMED OF A FIBROUS MATRIX FOR INTRALUMINAL DRUG DELIVERY

BACKGROUND OF THE INVENTION

1. Field of the Invention

The present invention generally relates to an intraluminal catheter device for use in angioplasty and delivery of a therapeutic agent. Particularly, the present invention is directed to a catheter having an expandable member having a therapeutic agent disposed thereon and a fibrous matrix covering for delivering a therapeutic agent.

2. Description of Related Art

The systemic administration of therapeutic agents, such as by transoral or intravenous means, treats the body as a whole even though the disease to be treated may be localized. In some cases, systemic administration may not be desirable because the therapeutic agents may have unwanted effects on parts of the body which are not to be treated, or because treatment of the diseased part of the body requires a high concentration of a therapeutic agent that may not be achievable by systemic administration.

It is therefore often desirable to administer therapeutic agents at localized sites within the body. Common examples include cases of localized vascular disease (e.g., heart disease) or diseased body lumens. Among the treatments becoming available for local treatment of vascular disease, are drug-eluting balloons. This type of medical device is typically a percutanueous transluminal coronary angioplasty (PTCA) balloon catheter that carries a therapeutic agent on the surface of the balloon for delivery to the vessel wall. The method generally includes the steps of adding a therapeutic agent to the balloon surface using any of a number of manufacturing processes, such as dip coating, spray coating, painting or pipetting onto the balloon, electron ion deposition, or plasma gamma discharge deposition, inserting the catheter into a blood vessel to a desired location, and expanding the catheter balloon against the surrounding tissue to allow the release of the drug.

In these cases, the therapeutic agent disposed on the balloon surface is exposed to the surrounding environment. As a result, it may contact the vascular surface as the device is tracked through the vessel to the treatment site, resulting in loss of the therapeutic agent and a reduced dose of the therapeutic agent to the target site. A further drawback is the premature diffusion of the drug during delivery into the body.

In view of the potential drawbacks to conventional drug delivery techniques, there exists a need for a device and method for the controlled, localized delivery of therapeutic agents to target locations or lesions within a mammalian body, while preventing the premature release or removal of the therapeutic agent during delivery.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a catheter device provided for intraluminal delivery of at least one therapeutic agent within a lumen or by contacting the vessel wall. Particularly, the catheter device includes an elongated catheter shaft having a proximal end portion and distal end portion and an inflation lumen disposed between the proximal end portion and the distal end portion. The catheter device includes an expandable member disposed proximate to the distal end of the catheter shaft, the expandable member having a therapeutic agent disposed on at least one portion of the outer surface of the expandable member. The catheter device further includes a covering which is positioned over at least one portion of the expandable member. Preferably, the covering is positioned over the portion of the expandable member that has the therapeutic agent disposed thereon. The covering is formed of a matrix of fiber elements which is configured to protect the therapeutic agent and prevent premature elution of the therapeutic agent as the catheter device is delivered to the target site. The fibers are formed from polymers, such as for example, but not limited to, polyamides, polyurethanes, silicone modified polyurethanes, fluoropolymers, polyolefins, polyimides, polyimines, (methyl)acrylic polymers, polyesters, polyglycolide, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly($\epsilon$-caprolactone) (PCL), polydioxanone, poly(ethylene glycol) (PEG), poly(vinyl alcohol), and co-polymers thereof.

The therapeutic agent is applied to the surface of the expandable member using coating processes, including but not limited to spray coating or dip coating. In accordance with one embodiment of the invention, following application of the therapeutic agent the expandable member can be folded or partially folded into a low profile configuration. The therapeutic agent can be selected from, but is not limited to, anti-proliferatives, anti-inflammatories, antineoplastics, anti-platelets, anti-coagulants, anti-fibrins, antithrombotics, antimitotics, antibiotics, antiallergics and antioxidant compounds and combinations thereof.

It is contemplated that in an alternative embodiment the expandable member may also be used to deliver angiogenic factors. Growth factors, such as isoforms of vasoendothelial growth factor (VEGF), fibroblast growth factor (FGF, e.g., beta-FGF), Del 1, hypoxia inducing factor (HIF 1-alpha), monocyte chemoattractant protein (MCP-1), nicotine, platelet derived growth factor (PDGF), insulin-like growth factor (HGF), estrogens, folliostatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). In some embodiments, angiogenic factors include, but are not limited to, peptides, such as PR39, PR11, and angiogenin, small molecules, such as PHD inhibitors, or other agents, such as eNOS enhancers.

In accordance with the invention, the protective covering formed of a matrix of fiber elements is positioned over the expandable member. Preferably, the protective covering is positioned over the area of the expandable member having the therapeutic agent disposed thereon. In accordance with one embodiment of the invention, the protective covering is essentially free of therapeutic agent. Essentially, the therapeutic agent is applied on the expandable member and the fibrous covering is positioned over the expandable member. The method of applying the therapeutic agent and positioning the fibrous covers over the expandable member is such that the therapeutic does not enter the fibrous matrix. Preferably, the matrix of fibers in the covering is relatively tightly woven to prevent the therapeutic agent from entering between the fibers.

In accordance with a preferred embodiment of the invention, the matrix of fiber elements are formed by an electrospinning process. Electrospinning is a method based on the ability of an electric field to overcome the surface tension of a polymer or biomacromolecule solution (or melt), and form a conical shape called the Taylor cone. Depending on the solution and process parameters such as polymer concentration, molecular weight, nozzle diameter, charge magnitude, spinning distance, and solution feed rate, continuous fibers can be produced that can have diameters ranging from a few hundred nanometers to several microns.

In accordance with the invention, the protective covering can be formed separately as a sleeve or conduit and is then slipped over the expandable member. In accordance with a preferred embodiment, the expandable member is folded or partially folded and the protective member is positioned over the folded balloon. The protective covering is positioned over at least one portion of the expandable member having a therapeutic agent coated thereon.

In accordance with the invention, the protective covering can be formed directly on the expandable member. In accordance with a preferred embodiment the expandable portion of the intraluminal catheter is positioned beneath the nozzle of an electrospinning apparatus in order to direct an electrospun fiber toward the expandable member and catheter shaft. In certain embodiments, the catheter is positioned adequately distant from the electrospinning nozzle to ensure that the electrospun fibers are able to dry as they travel the gap toward the catheter device. The portion of the protective covering that is disposed proximal and distal to the working length of the expandable member can subsequently be bonded to the catheter device.

In accordance with the invention, the catheter device can be used in connection with methods of delivering therapeutic agent. In certain embodiments the catheter is first advanced through the vasculature until the expandable member is positioned adjacent to the target disease or desired treatment site. Inflation fluid is then introduced through the catheter body and into the expandable member to expand or inflate the expandable member. Expansion of the expandable member causes the protective covering to expand. As expansion of the fibrous matrix occurs, the tightly woven fibers will stretch and gaps between the fibers will expand in size and shape to form channels. The therapeutic agent coated on the surface of the expandable member is delivered through the channels and into the vasculature or surrounding areas. In one preferred embodiment, the method of delivering therapeutic agent includes diffusion of the therapeutic agent from the channels in the protective covering to the vessel wall when the expandable member is expanded against the vessel wall. An alternative embodiment involves a burst release technique, wherein protective covering is expanded or stretched as the expandable member is expanded and the therapeutic agent is thereby released through the channels from the fiber matrix and into the vessel wall and surrounding area.

In accordance with certain embodiment of the invention, the outer surface of the expandable member is textured to include a plurality of voids. The voids can be configured to serve as areas or locations for loading a therapeutic agent onto the surface of the expandable member and can be introduced during the manufacture of the expandable member. In certain embodiments, the voids formed during the blowing process, however, the voids may be formed at any point during the manufacturing process of the expandable member, such as after the expandable member tubing extrusion or after the expandable member blowing step. Suitable methods of creating such voids or roughnesses to achieve the purpose of this invention include modification of the expandable member mold and/or modification of the expandable member itself via laser machining, laser ablation, micromachining, chemical etching, electrical discharge machining (EDM), photo-etching, photolithography, electron-beam patterning, and other methods that are well known in the art for modifying the surface of a metal mold and/or a polymer.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the product and method of the invention. Together with the description, the drawings serve to explain the principles of the invention.

DETAILED DESCRIPTION OF THE PREFERRED EMBODIMENT

Reference will now be made in detail to the present preferred embodiments of the invention. The method and corresponding steps of the invention will be described in conjunction with the detailed description of the intravascular catheter device.

In accordance with the present invention, an intraluminal catheter device is provided for delivery of at least one therapeutic agent within a lumen by contacting the vessel wall. Particularly, the catheter device includes an elongated catheter shaft having a proximal end portion and a distal end portion and an expandable member located proximate to the distal end portion of the catheter shaft, the expandable member having a therapeutic agent disposed on at least one portion of the surface and a covering positioned over the expandable member.

The expandable member contains a therapeutic agent disposed on at least one portion of the outer surface. Following application of at least one therapeutic agent to the outer surface of the expandable member, the protective covering is positioned over the expandable member. There are several embodiments for positioning the protective covering over the outer surface of the expandable member which will be discussed in detail herein. The protective covering is configured and positioned over at least one portion of the therapeutic covering. Preferably, the protective covering is positioned over the portion of the expandable member, preferably a balloon, that is generally cylindrical after balloon expansion and includes a therapeutic agent coating. In accordance with a preferred embodiment of the invention, the protective covering is essentially free of therapeutic agent. The protective covering and expandable member are configured such that the therapeutic agent does not enter or migrate into the protective covering or between the fibers of the protective covering. The catheter is configured for delivery through an anatomy and to a target treatment site. In accordance with one embodiment of the invention, once positioned near the target treatment site, the expandable member is inflated and the matrix of fiber elements of the covering also expands. As this occurs, the fibers of the covering will stretch and create gaps. The therapeutic agent is then delivered through the plurality of gaps that are defined between the fibers upon expansion of the expandable member. Therefore, the therapeutic agent is delivered to the diseased site and provides a beneficial effect. In one embodiment, the expandable member can contact the vasculature wall upon expansion and the therapeutic agent is delivered to the vessel wall.

Figure 1:
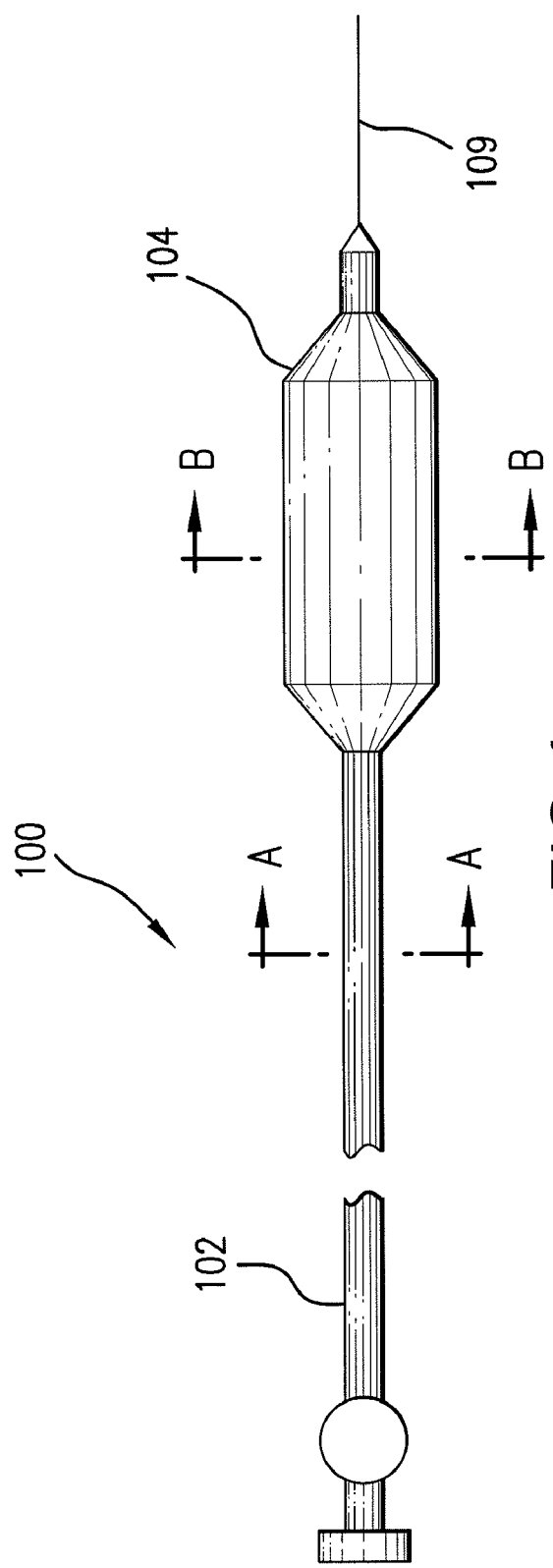
FIG. 1 is a planar view of a catheter having an expandable member and a covering in accordance with the invention.
Figure 2:
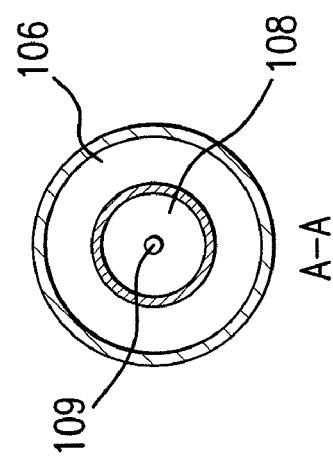
FIG. 2 is a cross-sectional view taken along lines A-A in FIG. 1 in accordance with one embodiment of the invention.
Figure 3:
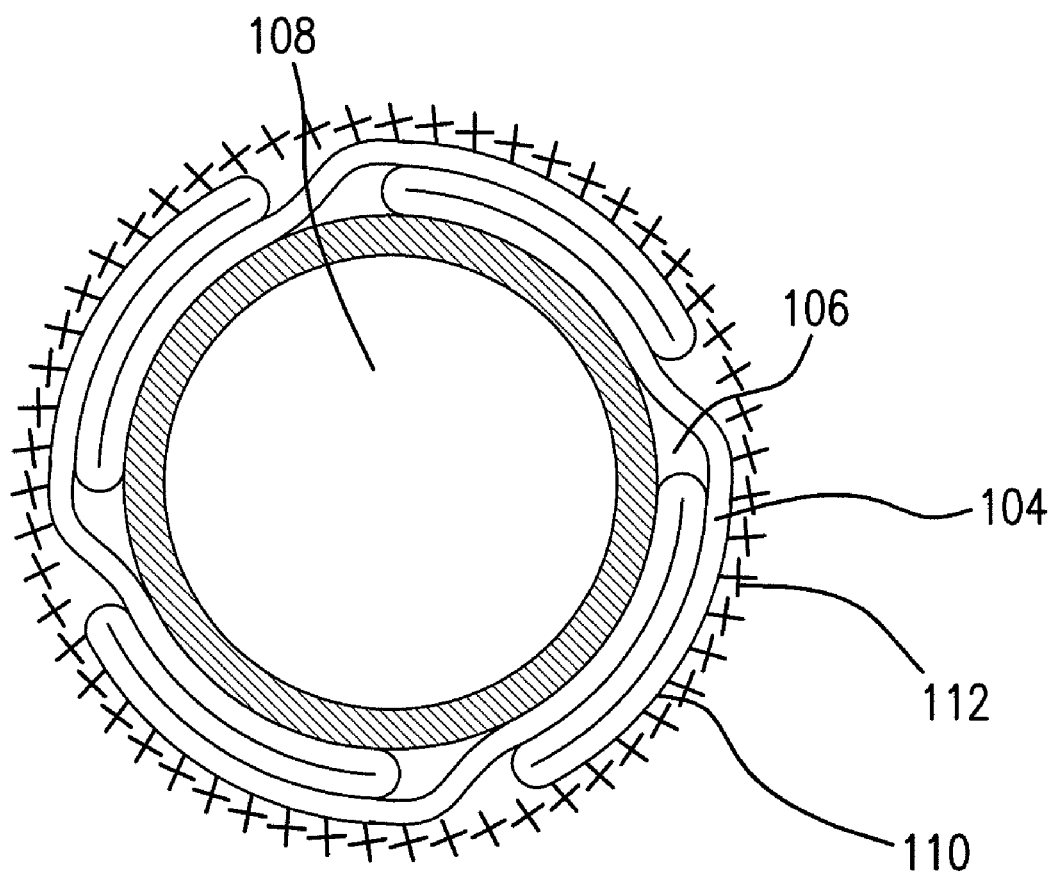
FIG. 3 is a cross-sectional view taken along lines B-B in FIG. 1 in accordance with one embodiment of the invention.

An exemplary embodiment of the intravascular catheter device in accordance with the present invention is shown schematically in FIGS. 1, 2 and 3. As shown in FIGS. 1, 2 and 3, the intraluminal medical device 100 generally includes an elongated catheter shaft 102 having a proximal end and having a distal end and an expandable member 104 located proximate to the distal end of the catheter shaft. The expandable member has an outer surface and an inner surface disposed at the distal end portion of the catheter shaft. An inflation lumen 106 can be disposed between the proximal end portion and the distal end portion of the catheter shaft 102. The expandable member 104 is placed in fluid communication with the inflation lumen 106. The inflation lumen can supply fluid under pressure, and establish negative pressure, to the expandable member. The expandable member 104 can thus be inflated and deflated. The elongated catheter is sized and configured for delivery through a tortuous anatomy, and can further include a guidewire lumen 108 that permits it to be delivered over a guidewire 109. The guidewire lumen can have an over-the-wire (OTW) or rapid-exchange (RX) construction, as is well known in the art. Alternatively, the catheter body can include a fixed guidewire to permit the catheter to be delivered to a vessel location without the use of a separate guidewire.

As illustrated in FIG. 3 and in accordance with the invention, the expandable member 104 has at least one therapeutic agent 110 disposed on at least one portion of the outer surface of the expandable member 104. The therapeutic agent 110 can be directly applied to the surface of the expandable member 104. For example and not limitation, the therapeutic coating 110 can be applied by techniques including powder coatings, spray coating, dip coating, pad printing, transfer by rolling, electrografting, and electrostatic coating, as understood in the art. The therapeutic agent can be coated over a portion or the entirety of the expandable member 104.

In accordance with one embodiment of the invention, following application of a therapeutic agent to the surface of the expandable member, the expandable member can be folded or alternatively, partially folded, into a low profile configuration. The expandable member can be folded using various techniques well known to those skilled in the art. The folding process may result in an expandable member with several folds, including but not limited to, three, four of five folds. By way of example, and not of limitation, certain exemplary folding processes that may be used in conjunction with the instant invention are described in U.S. Pat. No. 6,988,881, which is hereby expressly incorporated by reference in its entirety.

In accordance with the invention, the expandable member has a covering formed of a matrix of fiber elements 112 positioned over at least one portion of the expandable member 104. The covering 112 prevents the therapeutic agent from being prematurely released from the surface of the expandable member and therefore promotes an effective and accurate dosing. The covering is formed of a matrix of fiber elements. In accordance with the invention, the covering is positioned over the portion of the expandable member which has a therapeutic agent coated thereon. In accordance with one embodiment of the invention, the covering formed by a matrix of fiber elements can be formed by electrospinning of the fibers into a matrix configuration. Alternatively, the covering positioned over expandable member can be fabricated by melt-blowing or spunbonding processes to create the fibrous matrix.

The matrix configuration allows for a highly accessible surface area and therefore provides for an effective covering which prevents elution and wash-out of the therapeutic agent prior to reaching the target therapeutic site. The protective covering essentially separates the surface of the expandable member from the surrounding environment. Typically, the diameter of the fibers range from nano to micro in size preferably from 20 nanometers to 20 micrometers, more preferably from 200 nanometers to 2 micrometers. The fiber elements are configured to achieve a desired thickness of the protective covering. In accordance with a preferred embodiment of the invention, the thickness of the protective covering ranges from 1 micrometer to 500 micrometers, and preferably from 5 micrometers to 50 micrometers, based on the fiber size and number of layers deposited.

In accordance with the invention there are several embodiments for applying or positioning the protective covering over at least one portion of the expandable member. Preferably, the protective covering is positioned over the portion of the expandable member having the therapeutic agent disposed thereon.

Figure 4A:
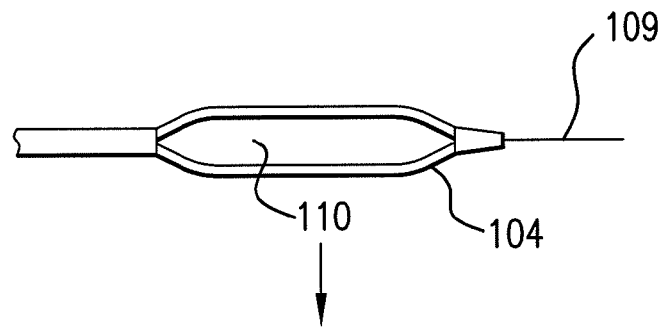
FIGS. 4a, 4b, 4c and 4d are planar views of a catheter having an expandable member and a fibrous covering in accordance with one embodiment of the invention.
Figure 4B:
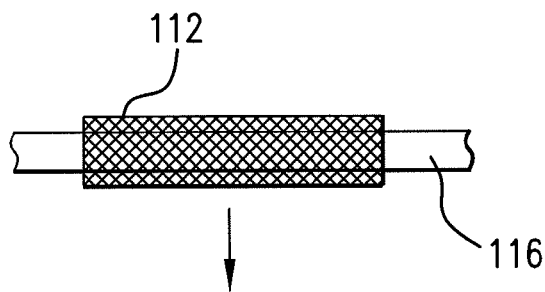

As illustrated in FIGS. 4a, 4b, 4c and 4d and in accordance with the invention, the protective covering is formed separately and is then slipped over the expandable member. As illustrated in FIG. 4a, an expandable member having a therapeutic agent coated thereon is formed as described above. The protective covering 112 formed of a matrix of fiber elements is then formed as a conduit or sleeve separate and apart from the fabrication of the expandable member. In accordance with one embodiment and as illustrated in FIG. 4b, for purposes of illustration and not limiation, fiber elements can be applied to a forming mandrel to form a matrix which preferably conforms in shape to that of the expandable member. The fiber elements can be applied to a forming mandrel using techniques and materials that are well known in the art. Such techniques to create a fibrous matrix, include but are not limited to, electrospinning processes and melt-blowing or spunbonding processes. In one embodiment, the mandrel diameter can be slightly larger than the diameter of the expandable member, preferably in a folded configuration, in order to permit the protective covering to be slipped over the expandable member. Alternatively, however, if the fibrous matrix is constructed from a sufficiently flexible material then over-sizing of the mandrel is not necessary.

Figure 4C:
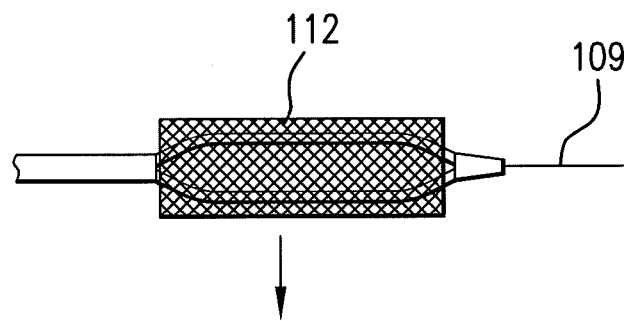
Figure 4D:
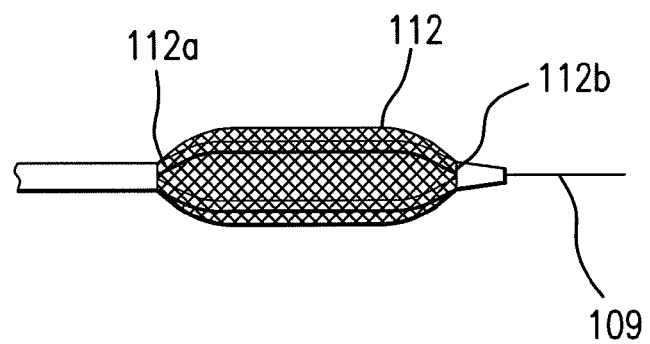

As illustrated in FIG. 4c, the protective coating is positioned over the expandable member. In accordance with a preferred embodiment of the invention, the expandable member is folded into a low profile configuration prior to positioning the covering. Preferably, the protective coating is positioned over at least one portion of the expandable member having a therapeutic agent disposed thereon. Accordingly, the protective coating prevents premature elution of the drug. In accordance with one embodiment of the invention and as illustrated in FIG. 4d, the protective coating has a proximal end portion 112a and a distal end portion 112b. Preferably, the protective covering is adhered to the expandable member by attaching at least one of the proximal end or distal end portions of the protective covering to the expandable member. Either the proximal end or distal end portions are attached to the expandable member at positions proximal and distal to the working length of the expandable member. The "working length" of the expandable member, preferably a balloon, is defined as the portion that is generally cylindrical after inflation of the expandable member. Preferably, the working length of the expandable member includes a therapeutic agent coating. In one embodiment, the proximal end portion of the protective covering is attached at a position proximal to the portion of the expandable member that is generally cylindrical after expansion of the expandable member. In another embodiment, the distal end portion of the protective covering is attached at a position distal to the portion of the expandable member that is generally cylindrical after expansion of the expandable member. In yet another embodiment, both the distal and proximal end portions of the protective covering are attached to positions proximal and distal to the portion of the expandable member that is generally cylindrical after expansion of the expandable member. In yet another embodiment, at least one of the proximal or distal end portions of the protective covering is attached to the catheter shaft. The proximal or distal end portions of the protective covering are attached to the expandable member or the catheter shaft using various techniques known in the art, including but not limited to, adhesion, thermal welding, heat shrink bands and direct solvent bonding. In accordance with one embodiment, it may be necessary to reduce the diameter of the protective covering in order to create a thermal weld using a laser or another heat source as is well known in the art. Alternatively, heat shrink bands can be used at the bonding locations to attach the protective covering. Another method includes using directed solvent bonding to weld the locations. The direct solvent bonding technique further reduces the profile of the protective covering and enables a secure bond to be formed. In accordance with another embodiment, it is also possible to reduce the diameter of the covering by twisting it in a candy-wrapper fashion to bring the protective covering closer to positions proximal or distal to the working length of the expandable member and/or the catheter shaft and further enable a secure bond to be formed.

Figure 5A:
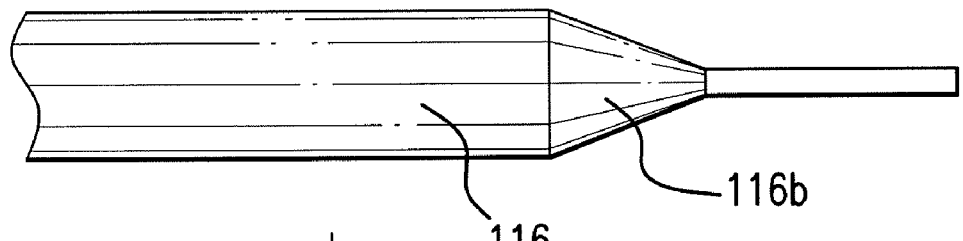
FIGS. 5a, 5b and 5c are planar views of a catheter having an expandable member and a fibrous covering in accordance with another embodiment of the invention.
Figure 5B:
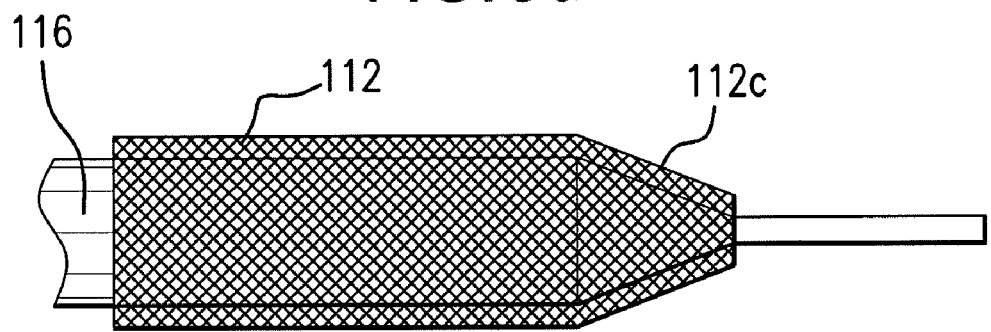
Figure 5C:
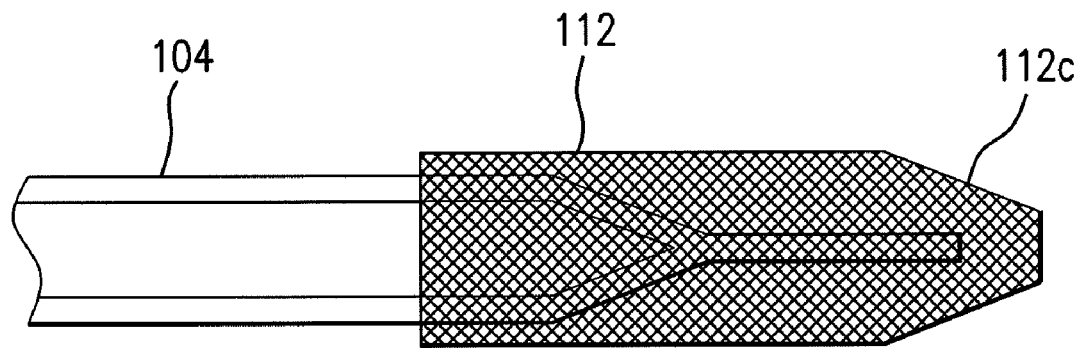

As illustrated in FIGS. 5a, 5b and 5c, and in accordance with another embodiment of the invention, the protective covering is formed separately with tapered ends and is then slipped over the expandable member having a therapeutic agent coated thereon. The protective covering 112 formed of a matrix of fiber elements is formed as a conduit or sleeve. In accordance with one embodiment, the fiber elements can be applied to a forming mandrel 116 to form a matrix which preferably conforms in shape to that of the expandable member. In accordance with one embodiment of the invention and as illustrated in FIG. 5a, at least one end of the mandrel 116b is slightly tapered in order to form a protective covering with at least one tapered end. The tapered end will result in an inner diameter of an end portion that more closely matches the diameter of a position proximal or distal to the working length of the expandable member or the diameter of the catheter shaft. Accordingly, adhering the protective covering to the catheter shaft or the expandable member will be easier, since there will be less gap to close with an adhesive, or less need to reduce the diameter of the protective covering during welding process. As illustrated in FIG. 5b, the fiber elements can be applied to a forming mandrel using techniques and materials that are well known in the art. Such techniques to create a fibrous matrix, include but are not limited to, electrospinning processes and melt-blowing or spunbonding processes. In one embodiment, the mandrel diameter can be slightly larger than the diameter of the expandable member, preferably in a folded configuration, in order to permit the protective covering to be slipped over the expandable member. Alternatively, however, if the fibrous matrix is constructed from a sufficiently flexible material then over-sizing of the mandrel is not necessary.

As illustrated in FIG. 5c, the protective covering is positioned over the expandable member such that at least one tapered end of the protective covering contacts the tapered portion of the expandable member. Preferably, the protective coating is positioned over at least one portion of the expandable member having a therapeutic agent disposed thereon. Accordingly, the protective coating prevents premature elution of the drug. The protective coating has a proximal end portion and a distal end portion, at least one of which is tapered. The protective covering is adhered to the expandable member by attaching at least one of the proximal end or distal end portions of the protective covering to the expandable member. Either the proximal end or distal end portions are attached to the expandable member at positions proximal and distal to the working length of the expandable member. Preferably, the working length of the expandable member includes a therapeutic agent coating. In one embodiment, the proximal end portion of the protective covering is attached at a position proximal to the portion of the expandable member that is generally cylindrical after expansion of the expandable member. In another embodiment, the distal end portion of the protective covering is attached at a position distal to the portion of the expandable member that is generally cylindrical after expansion of the expandable member. In yet another embodiment, both the distal and proximal end portions of the protective covering are attached to positions proximal and distal to the portion of the expandable member that is generally cylindrical after expansion of the expandable member. In yet another embodiment, at least one of the proximal or distal end portions of the protective covering is attached to the catheter shaft. The proximal or distal end portions of the protective covering are attached to the expandable member or the catheter shaft using various techniques known in the art, including but not limited to, adhesion, thermal welding, heat shrink bands and direct solvent bonding. In accordance with one embodiment, it may be necessary to reduce the diameter of the protective covering at an untapered end in order to create a thermal weld using a laser or another heat source as is well known in the art. Alternatively, heat shrink bands can be used at the bonding locations to attach the protective covering. Another method includes using directed solvent bonding to weld the locations. The direct solvent bonding technique further reduces the profile of the protective covering and enables a secure bond to be formed. In accordance with another embodiment, it is also possible to reduce the diameter of the covering by twisting it in a candy-wrapper fashion to bring the protective covering closer to positions proximal or distal to the working length of the expandable member and/or the catheter shaft and further enable a secure bond to be formed.

Figure 6:
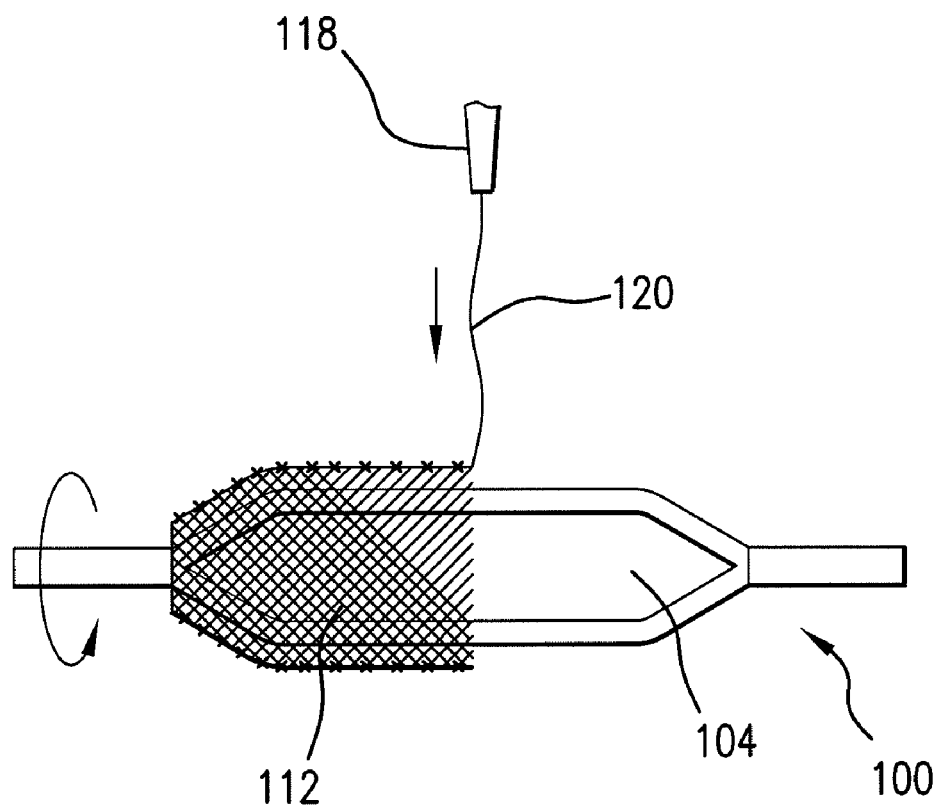
FIG. 6 is a schematic drawings of an exemplary electrospinning process used to form the expandable member of the present invention.

As illustrated in FIG. 6 and in accordance with another embodiment of the invention, the protective covering 112 is electrospun directly onto the surface of the expandable member having a therapeutic agent coated thereon. The expandable portion of an intraluminal catheter is positioned beneath the nozzle 118 of an electrospinning apparatus in order to direct an electrospun fiber 120 toward the expandable member 104 and catheter shaft. The catheter device 100 is positioned adequately distant from the electrospinning nozzle 118 to ensure that the electrospun fibers 120 are able to dry as they travel the gap toward the catheter device. Drying of the electrospun fibers occurs through the evaporation of the solvent that the electrospun fibers are dissolved within. In accordance with the invention, a fiber matrix is electrospun over the working length of the expandable member and a portion of the device proximal and distal to the working length of the expandable member. The portion of the protective covering that is disposed over the portions that are proximal and distal to the working length of the expandable member will subsequently be bonded to the device. Accordingly, it is preferred to make the distal and proximal end portions of the protective covering match the profile of the expandable member as closely as possible.

The proximal or distal end portions of the electrospun protective covering are attached to the expandable member or the catheter shaft using various techniques known in the art, including but not limited to, adhesion, thermal welding, heat shrink bands and direct solvent bonding. Additionally or alternatively, the distance between the electrospinning nozzle and the device may be shortened when the fiber is ejected toward the distal and proximal portions of the working length of the expandable member. Therefore, the solvent will not evaporate as fully before the fibers reach the device and the fibers will adhere to the surface of the expandable device as the solvent evaporates when the fiber and the surface are in contact. Any combination of the methods discussed herein may be used to adhere the electrospun protective covering to the surface of the expandable member Although FIG. 6 is directed to a process for directly forming a covering formed of a matrix of fiber elements onto the surface of an expandable member using an electrospun process, any process that can form a matrix of fiber elements directly onto the surface of the catheter device can be used in accordance with the invention. Such processes include but are not limited to melt-blowing or spunbond processes.

Any suitable process for forming a protective covering from a matrix of fiber elements can be used in accordance with the present invention. As discussed above, the protective covering is a shaped structure formed from many fibers that exist in a matrix configuration. As a result of the matrix-like configuration which is tightly woven and overlapped, the protective covering prevents premature elution of a therapeutic agent from the surface of an expandable member. Suitable processes for creating the fibrous matrix which is formed into a protective covering include, for example, electrospinning, melt-blowing or spunbonding.

In accordance with the invention, the protective covering is essentially free of any therapeutic agent. The method of applying the therapeutic agent and positioning the fibrous covers over the expandable member is such that the therapeutic does not enter the fibrous matrix. Preferably, the matrix of fibers in the covering is relatively tightly woven to prevent the therapeutic agent from entering between the fibers.

As a result of the overlapping matrix configuration of the fiber elements, small gaps are present between the adjacent fibers of the matrix. The diameter of each fiber as well as the configuration of overlapping fibers will affect the gap size of the matrix since it essentially dictates the opening that exists between the fiber elements of the matrix. Processing parameters such as nozzle position and solution composition, among others, will also impact the gap size. the matrix may include gaps of similar or significantly different sizes throughout. In accordance with the invention, the gaps are sized and configured to prevent the therapeutic agent from entering between the fibers.

Figure 7:
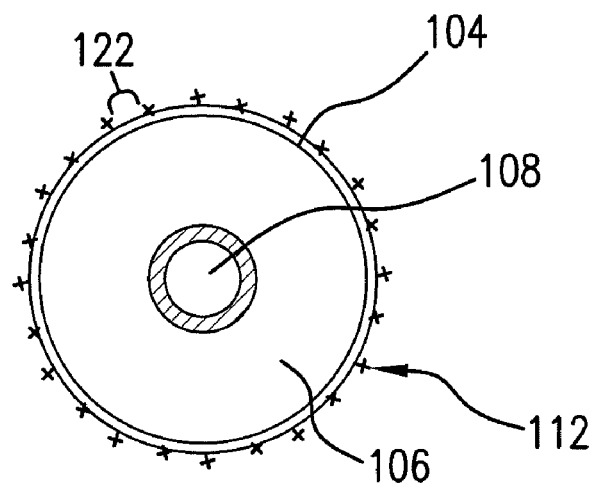
FIG. 7 is a cross-sectional view of the inflated expandable member having a fibrous covering in accordance with the present invention.

A method of use is therefore provided in accordance with this invention, the method having the following steps. The catheter is advanced through the vasculature until the expandable member is positioned adjacent to the target disease or desired treatment site. Inflation fluid is introduced through the catheter body and into the expandable member to expand or inflate the expandable member 104. As illustrated in FIG. 7, expansion of the expandable member will also cause the protective covering 112 to expand. As expansion of the fibrous matrix occurs, the tightly woven fibers will stretch and gaps between the fibers will expand in size and shape to form channels 122. The therapeutic agent 110 coated on the surface of the expandable member 104 is delivered through the channels 122 and into the vasculature or surrounding areas. One method of delivering the therapeutic agent includes diffusion of the therapeutic agent from the channels in the protective covering to the vessel wall when the expandable member is expanded against the vessel wall. Another method of delivery includes a burst release technique, wherein protective covering is expanded or stretched as the expandable member is expanded and the therapeutic agent is thereby released through the channels from the fiber matrix and into the vessel wall and surrounding area.

In accordance with one aspect of the invention, the expandable member is configured to provide a radial force against the vessel wall during expansion. In one embodiment, the expansion allows the expandable member to contact the vessel wall and the therapeutic agent to be delivered into the vessel wall at the target treatment site. This radial force ensures that the expandable member can expand safely, without causing harm to the vessel wall. Additionally, reducing the stress in the vessel wall can also contribute to a higher rate of uptake of therapeutic agent within the vessel wall as well as improved retention of the therapeutic agent after the catheter has been delivered and removed.

For purpose of illustration and not limitation, the expandable member fabricated from one or more polymers (e.g., a mixture of polymers). For example, the polymers can include one or more thermoplastics and/or thermoset polymers. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers, and silicones. Other examples of thermosets include epoxies and isocyanates. Biocompatible thermosets may also be used. Biocompatible thermosets include, for example, biodegradable polycaprolactone, poly(dimethylsiloxane) containing polyurethanes and ureas, and polysiloxanes. Ultraviolet curable polymers, such as polyimides, can also be used. Other examples of polymers that can be used to fabricated the expandable member include polyethylenes, polyethylene ionomers, polyethylene copolymers, polyetheretherketone (PEEK), thermoplastic polyester elastomers (e.g., Hytrel®)), and combinations thereof. The expandable member can include multiple layers provided, for example, by coextrusion.

The expandable member can be formed using any suitable technique, such as blow molding, film molding, injection molding, and/or extrusion. For example, a polymer tube can be extruded, and can thereafter be stretched and blown to form a balloon. Methods of forming an expandable member from a tube are described, for example, in U.S. Pat. No. 6,120,364 to Anderson; U.S. Pat. No. 5,714,110 to Wang; and U.S. Pat. No. 4,963,313 to Noddin, the disclosures of which are incorporated in their entirety by reference herein.

In accordance with the invention, the covering is formed of a matrix of polymeric fibers. The polymeric material of the fiber include, but are not limited to, polyamides, polyurethanes, fluoropolymers, polyolefins, polyimides, polyimines, (methyl)acrylic polymers, polyesters, polyglycolide (PGA), poly(L-lactide) (PLLA), poly(D,L-lactide) (PDLLA), poly (L-lactide-co-glycolide) (PLGA), poly(D,L-lactide-co-glycolide) (PDLGA), poly(ε-caprolactone) (PCL), polydioxanone, poly(ethylene glycol) (PEG), polyvinyl alcohol), and suitable copolymers thereof, poly(ester amides) (PEA), and biodegradable elastomers such as biodegradable poly(ester urethanes) (PEU), polyhydroxyalkanoates such as poly(4-hydroxybutyrate) or poly(3-hydroxybutyrate), poly(1,3-trimethylene carbonate). Alternatively, the fiber can be a combination of one or more polymeric materials.

In accordance with one embodiment of the invention, the plurality of fibers can include at least one coating completely or partially surrounding the polymeric core. The coating comprises a material that acts as a protective coating for the covering and further prevents premature elution of the therapeutic agent prior to proper placement within the vessel lumen at a treatment site. Preferably, this protective layer prevents physical damage to the covering formed of a matrix of fiber elements layer during insertion. In accordance with a preferred embodiment of the invention, the protective coating comprises a protective substance that is dissolvable, biodegradable or disintegrable upon expansion or inflation of the expandable member. For purpose of illustration and not limitation, the protective substance includes glucose, hydrophilic substances, biodegradable substances, contrast mediums, mediums which are dissolvable in blood or aqueous mediums, or other mediums which will crack under expansion and will therefore allow the therapeutic agent to contact the vessel wall.

As illustrated in FIG. 3, the therapeutic agent 110 can be directly applied to the surface of the expandable member 104. For example and not limitation, the therapeutic coating 110 can be applied by techniques including powder coatings, spray coating, dip coating, pad printing, transfer by rolling, electrografting, and electrostatic coating, as understood in the art. The therapeutic agent can be coated over a portion or the entirety of the expandable member 104. The method of applying the therapeutic agent and positioning the fibrous covers over the expandable member is such that the therapeutic does not enter the fibrous matrix.

In accordance with one embodiment of the invention, the therapeutic agent is coated over a portion or the entirety of the outer surface of the expandable member, the outer surface being generally smooth. Accordingly, the therapeutic agent is disposed as a layer having a definable thickness on the outer surface of the expandable member.

Figure 8:
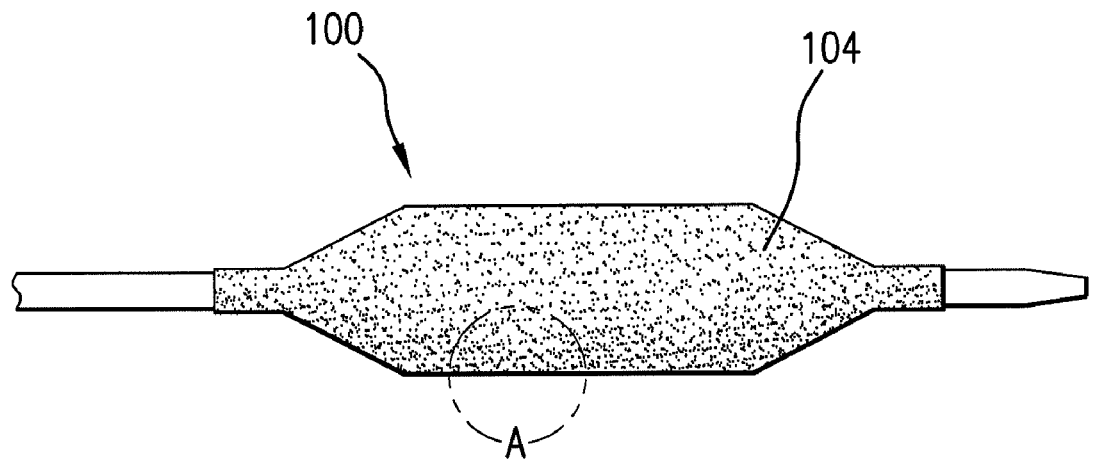
FIG. 8 is a planar view of an expandable member having a plurality of voids in accordance with another embodiment of the invention.
Figure 9:
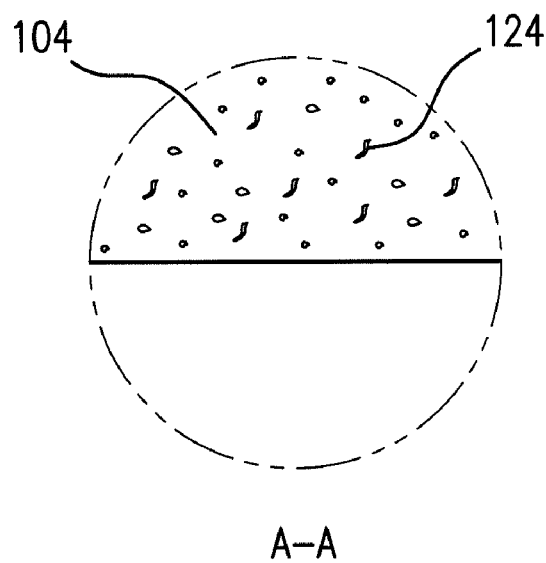
FIG. 9 is an expanded view of detail "A" in FIG. 8 in accordance with an embodiment of the invention.
Figure 10:
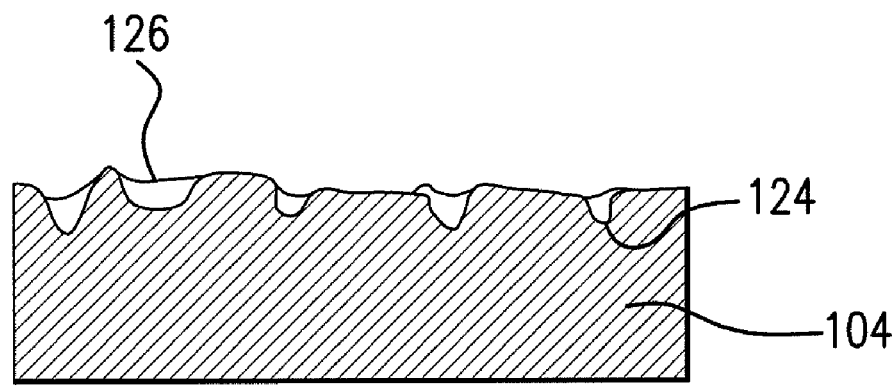
FIG. 10 is a view of the expandable member of FIG. 8 having therapeutic agent loaded thereon.

However, in accordance with an alternative embodiment of the invention, as illustrated in FIGS. 8, 9, and 10, the outer surface of the expandable member is textured to include a plurality of voids. The voids are configured to serve as areas or locations for loading a therapeutic agent onto the surface of the expandable member. The voids are introduced during the manufacture of the expandable member. The voids are also referred to as nano- or micro-roughness.

As illustrated in FIGS. 8 and 9, the expandable member 104 includes a plurality of voids 124 introduced into the surface of the expandable member. During the manufacturing process, the voids are introduced into the surface of the expandable member. Preferably, the voids are formed during the blowing process, however, the voids may be formed at any point during the manufacturing process of the expandable member, such as after the expandable member tubing extrusion or after the expandable member blowing step. As illustrated in FIG. 9, introduction of these voids or roughnesses provides a location for creating a deposit of therapeutic agent wherein the therapeutic agent is loaded on the surface of the expandable member.

In accordance with the invention, suitable methods of creating such voids or roughnesses to achieve the purpose of this invention include modification of the expandable member mold and/or modification of the expandable member itself via laser machining, laser ablation, micromachining, chemical etching, electrical discharge machining (EDM), photo-etching, photolithography, electron-beam patterning, and other methods that are well known in the art for modifying the surface of a metal mold and/or a polymer. Laser types that would be useful for laser machining of the expandable member's surface include but are not limited to femto-second lasers, picosecond lasers and excimer lasers that would limit the heat affect on the material surrounding the microroughnesses. Etching can be accomplished using a suitable etchant, such as sulfuric acid on the surface of an expandable member formed from nylon.

In accordance with the invention, the roughness of the surface of the expandable member can be controlled by forming an expandable member mold with a roughened surface. During the expandable member blowing process, the outer surface of the expandable member will contact and generally form to these expandable member surface characteristics, thereby creating permanent roughnesses within the surface of the expandable member that closely match the roughness of the expandable member molds. This process essentially transfers the inverse of the expandable member mold roughness to the outer surface of the expandable member, and therefore the roughness of the expandable member can be controlled by controlling the mold roughness. Validation of what roughness wavelengths transfer can be achieved is accomplished by measuring the roughness of the expandable member mold after patterning and by measuring the roughness of the expandable member to determine transfer of the mold pattern. One method of measurement would be to utilize a non-contact profilometer such as, for example, the Veeco optical profilometer. These measurements can further be manipulated using Fourier transformation to understand what roughness wavelengths are present. Testing can be performed to understand the effect of those wavelengths, and the mold may be further manipulated to refine those wavelengths to ones that are shown to be more desirable.

As illustrated in FIG. 10, after creating the microroughnesses or voids on the surface of the expandable member, a therapeutic agent may be applied to the surface of the expandable member. The therapeutic agent may be applied using processes as described herein, including but not limited to, dip coating, spray coating, or electrical discharge coating. As the surface of the expandable member is coated the plurality of voids are filled with the therapeutic agent. In accordance with the invention, the balloon surface may be partially or completely coated with therapeutic agent. Accordingly, not every voids is necessarily filled with therapeutic agent.

In accordance with the invention, the plurality of voids range in size from the nanometer to micrometer range. Preferably, the plurality of voids range in size between 1 nanometer and 100 microns. More preferably, the plurality of voids range in size between 1 nanometer and 40 microns. Even more preferably, however, the plurality of voids range in size from 1 nanometer to 1 micron.

Following application of the therapeutic agent, the expandable member may be folded or partially folded into a low profile configuration prior to the step of positioning the protective covering formed of a matrix of fiber elements over at least one portion of the expandable member as described above.

Figure 11:
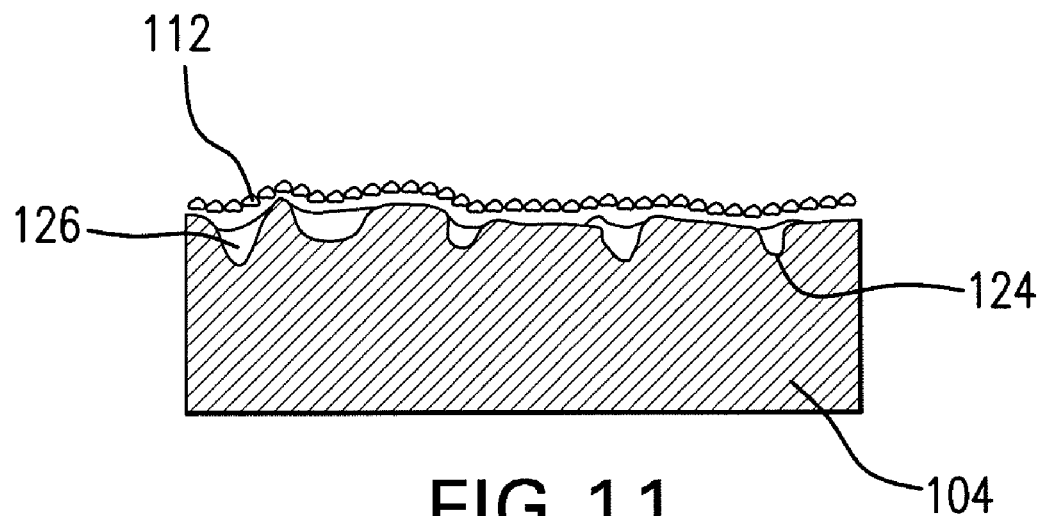
FIG. 11 is a view of the expandable member of FIG. 8 having a therapeutic agent loaded thereon and a protective covering disposed thereon.

As illustrated in FIG. 11, the protective covering 112 formed of a matrix of fiber elements is positioned over at least one portion of the expandable member 104. As illustrated in FIG. 11, the protective covering 112 is positioned over the outer surface of the expandable member 104 and contacts the surface of the expandable member above the plurality of voids. Therefore, the therapeutic agent, for the most part, does not come into contact with the protective covering. As illustrated in FIG. 11, the fibrous matrix 112 of the protective covering contacts the balloon surface, but not the interior surface of the voids. Therefore, the therapeutic agent is prevented from entering the fibers since the fibers are positioned along the peaks of the voids. Accordingly, the majority of the surface of the protective covering does not contact the therapeutic agent, and the protective covering is therefore essentially void of therapeutic material. Furthermore, the tightly packed fibrous matrix that forms the covering prevents any therapeutic agent from entering between the fibers. Accordingly, there is limited pressure on the agent to force wicking, and there are minimal pathways available for the agent to wick into.

In accordance with the invention, the protective covering formed from a fibrous matrix is disposed over the roughened surface to protect the therapeutic agent from premature elution within the patient anatomy during delivery. The therapeutic agent disposed within the voids or roughnesses will not leach between the fibers during delivery of the catheter device, but the therapeutic agent can be delivered through the channels that are formed during expansion of the fibrous matrix of the protective covering as the expandable member is inflated. During inflation of the expandable member, fibers of the protective covering are separated due to the increase in the surface area of the expandable member and channels are formed between the separated fibers. The therapeutic agent can therefore be delivered from the voids in the surface of the expandable member and through the channels in the fibers into the vessel wall and surrounding vasculature.

In accordance with yet another embodiment, a stent may be positioned over the expandable member having the protective covering thereon. Preferably, the stent is a bare metal stent.

In accordance with one embodiment of the invention, the therapeutic agent further comprises at least one excipient. Excipients include but are not limited to, contrast agents, polysaccharides, amino acids, proteins, non-ionic hydrophilic polymers, ionic hydrophilic polymers, acrylates, hydrophobic polymers, aliphatic polyesters and polyester block copolymers, mucoadhesives and plasticizers, For example and not limitation, at least one therapeutic agent can include anti-proliferative, anti-inflammatory, anti-neoplastic, antiplatelet, anti-coagulant, anti-fibrin, anti-thrombotic, antimitotic, antibiotic, antiallergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an anti-sense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that may be developed in the future for use with intraluminal catheter devices may likewise be used and all are within the scope of this invention.

For example and not limitation, the therapeutic agents effective in preventing restenosis, including those classified into the categories of anti-proliferative agents, anti-platelet agents, anti-inflammatory agents, anti-thrombotic agents, and thrombolytic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpI-IbIIIa or avb3, antibodies that block binding to gpIIaIIIb or avb3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agent. Non-limiting examples of anti-inflammatory agents include prednisone, dexamethasone, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, including, for example, anti-factor VII/VIIa antibodies, rNAPc2, and tissue factor pathway inhibitor (TFPI).

Thrombolytic agents, which can be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other therapeutic agents include cytotoxic drugs, including, for example, apoptosis inducers, including TGF, and topoisomerase inhibitors, including, 10-hydroxycamptothecin, irinotecan, and doxorubicin. Other therapeutic agents include drugs that inhibit cell de-differentiation and cytostatic drugs. The at least one therapeutic agent can also include anti-lipaedemic agents, including fenofibrate, matrix metalloproteinase inhibitors, including, for example, batimistat, antagonists of the endothelin-A receptor, including, for example, darusentan, and antagonists of the avb3 integrin receptor.

In accordance with another embodiment of the invention, the expandable member can include a liner disposed on at least one portion of the inner surface of the expandable member. Preferably the liner is non-permeable. The liner can assist in the expansion or inflation of the expandable member.

In accordance with a preferred embodiment of the invention, the protective covering is formed by an electrospinning process. Due to the wide variety of materials that can be used for the electrospinning process, the expandable member can be formed from a relatively soft material, which will improve deliverability of the device, and prevent damage to the anatomy during delivery. Additionally, the electrospinning process allows for the fibers to be formed with one or more coatings. In accordance with one embodiment, and as discussed above, the fibers can include a base material that supplies structure to the expandable member, and a first coating formed from one or more protective coatings. The protective coating can be dissolvable or disintegrable upon inflation of the expandable member.

In accordance with a preferred embodiment of the present invention, an exemplary method of electrospinning a protective covering is provided. As discussed above and illustrated in FIGS. 4b, 4c, 4d, 5a, 5b and 5c, the exemplary process of forming a protective covering includes providing a forming mandrel with a profile that is approximately the same as the desired profile of the protective covering. Material fibers are then electrospun onto the mandrel surface. Alternatively, however, as illustrated in FIG. 6, the material fibers can be electrospun directly onto the surface of the expandable member. For example, and not limitation, the electrospinning fibers are formed from polyurethane dissolved in a solvent such as acetone, tetrahydrofuran, N,N-dimethylformamide, chloroform, trifluoroethanol, hexafluoroisopropanol, or blends thereof. During the electrospinning process, the solvent begins to evaporate. When the electrospinning fibers reach the mandrel surface, the remainder of the solvent evaporates leaving the electrospun fibers. As the electrospinning layers are added, additional crossing of the electrospinning fibers will result in a dense matrix of material having radial channels or gaps passing therethrough. The size and location of these channels and gaps can be controlled through various process parameters, such as solution composition, nozzle position, and other parameters known in the art.

For example, U.S. Pat. Nos. 6,382,526 and 6,520,425 incorporated herein by reference in their entirety, are directed to a process and apparatus for the production of nanofibers. An electrospinning fixture is provided that includes a working stage for holding the mandrel or catheter device that the electrospun material matrix will be formed on. This stage should include rotational and axial movement capabilities and the motion of the stage is to be controlled by a motor synchronized with a motor controller. The stage includes a holding fixture such as a chuck that accepts the balloon member and transmits motion thereto. The holding fixture is also connected to the negative lead of a power source, making it the cathode of the electrolytic process. The positive lead of a power source is connected to the ejection nozzle, making the nozzle the anode of the electrolytic process.

Typically, electrospinning processes require high voltage but relatively low current. In one embodiment of this invention, the power source is capable of delivering 0 to 60 kilovolts of electrical potential, but generally operates in the range of 10 to 20 kilovolts during the electrospinning process. The current that is provided by the power source is generally in the 5 to 10 microampere range. It will be appreciated that these ranges can vary depending upon the electrospinning material and process parameters. Also, it can be preferable to utilize two power sources placed in parallel or in series, depending on the goals of the process.

The nozzle is connected to a reservoir filled with electrospinning material dissolved in a solvent, and is placed in fluid communication with the reservoir by a fluid transport lumen and a pump. The electrospinning material includes thermoplastic polymeric material discussed above in connection with the material of the expandable member. Suitable organic or aqueous based electrospinning solvents, include but are not limited to, acetone, methyl ethyl ketone, cyclohexanone, dichloromethane, chloroform, trifluoroethanol, hexafluoroisopropanol, tetrahydrofuran, N,N-dimethylformamide, ethyl acetate, isopropanol, ethanol, water or blends thereof. A particular embodiment of electrospinning material includes polyurethane dissolved in tetrahydrofuran, although this can be varied widely depending upon the requirements of the invention.

The nozzle can be located in a position that creates the desired electrospinning pattern. For example, if a random matrix pattern is desirable, the nozzle exit can be located greater than about 3 mm from the expandable member surface. If a more controlled pattern is desired, the nozzle can be located within about 3 mm from the expandable member surface. The nozzle exit inner diameter will typically be in the range of about 500 micrometer to 1.5 mm in order to achieve the desired electrospinning fiber size.

The electrospinning fiber will normally be ejected from the Taylor cone adjacent to the anode toward the cathode. The fibers will preferably have diameters in the range of about 20 nanometer to 10 micrometer. This size range will affect the gap size of the matrix since it will determine how much gap exists between overlapping fibers. The density of the fibers and the number of fiber layers will also affect the gap size. It is important to note that various changes to the electrospinning fibers can be made in accordance with this invention, which will affect the efficacy of the solution. For example, it is possible to electrospin a fiber that has two layers, a core (inner layer) and an outer coating (outer layer), by utilizing a specific capillary nozzle as shown in FIG. 7. This construction will form an electrospinning fiber that has, for example, a polyurethane core and a protective agent outer coating.

To maximize fiber bonding and minimize layer delamination within the electrospun expandable member, fabrication distance can be lowered to an appropriate value to cause fibers to lightly bond between layers due to presence of more solvent with less evaporation distance.

Further process variables such as polymer solution concentration as stated previously can also affect both morphology and fiber diameter. Increasing polymer concentration and solution viscosity while holding all other variables constant generally results in larger fiber diameter. Fiber diameters can then be varied from tens of nanometers to greater than a micron based on the parameters used. Wall thickness of the nanofiber protective covering could be controlled from tens of microns up to a millimeter or greater by adjusting fabrication time from a few minutes up to an hour or more. Fabrication parameters and material composition can also be optimized for each particular catheter delivery system, to allow for the desired radial force, flexibility and recoverability.

In accordance with another embodiment, the fibrous matrix which is formed into a protective covering is formed from a melt-blowing or spunbonding process. The melt blowing process is well known in the art and involves extruding a fiber-forming thermoplastic polymer resin in molten form through orifices of a heated nozzle into a stream of hot gas to attenuate the molten resin as fibers which form a fiber stream, the fibers being collected on a receiver in the path of the fiber stream to form a nonwoven web. The fibrous web can then be shaped into a protective covering. A method for producing a melt-blown fibrous web is described in U.S. Pat. No. 3,978,185 to Buntin et al., which is incorporated herein by reference in its entirety. The spunbonding process, equally well know in the art, is similar to the melt-blowing process, the two major differences between the two processes being i) the temperature and volume of the air used to attenuate the filaments and ii) the location where the filament draw or attenuation force is applied. A melt-blowing process uses large amounts of high-temperature air to attenuate the filaments. The air temperature is typically equal to or slightly greater than the melt temperature of the polymer. In contrast, the spunbonding process generally uses a smaller volume of air close to ambient temperature to first quench the fibers and then to attenuate the fibers. Methods for producing spunbonded webs are disclosed in U.S. Pat. Nos. 3,338,992 and 3,341,394 to Kinney; U.S. Pat. No. 3,276,944 to Levy; U.S. Pat. No. 3,502,538 to Peterson; U.S. Pat. Nos. 3,502,763 and 3,509,009 to Hartmann; U.S. Pat. No. 3,542,615 to Dobo et al. and U.S. Pat. No. 3,692,618 to Dorschner et al, the disclosures of which are incorporated herein by reference in their entirety. Both the melt-blowing and spunbonding processes can be used to produce fibers having a diameter of about 100 nanometers. Polymers that are suitable for use in the melt-blowing and spunbonding processes which can be used to form the protective covering include, but are not limited to polypropylene, polyethylene, polybutylene terephthalate, Nylon 6, Nylon 11, polycarbonate, polyurethanes, polyesters, poly(vinylidenefluoride) and poly(ester-amides).

Once formed, the fibrous matrix can be attached to an elongated catheter shaft by any conventional and suitable techniques so as to be in fluid communication with an inflation lumen. Similarly, the fibrous matrix can be folded or collapsed using known and suitable techniques for assembly, packaging, delivery and deployment as is known in the art.

The following examples are presented in order to more fully illustrate certain embodiments of the invention. These examples in no way, however, should be construed as limiting the broad scope of the invention. One skilled in the art can readily devise many variations and modifications of the principles disclosed herein without departing from the scope of the invention.

EXAMPLES

Figure 12A:
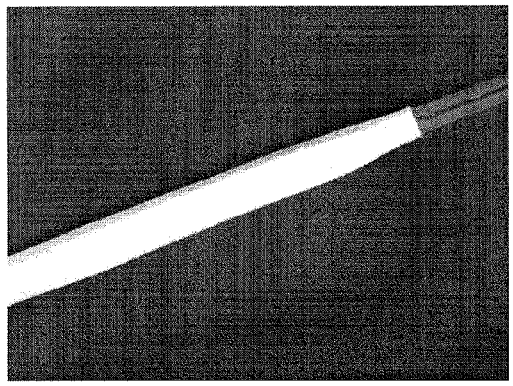
FIGS. 12a and 12b are macroscopic and cross-section views of an expandable member and a fibrous covering in accordance with one embodiment of the invention.
Figure 12B:
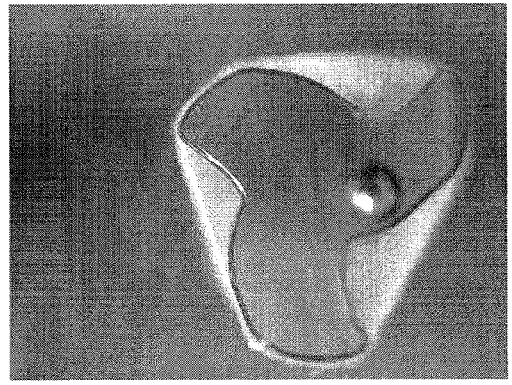

Example A 20 wt % PVDF in acetone was electrospun directly onto a Pellethane angioplasty balloon folded clockwise as shown in FIGS. 12a and 12b. Process parameters included a nozzle voltage of +10 kV and balloon mandrel voltage of −5 kV, a spinning distance of 4.0 cm, a solution flowrate of 1 mL/h for a volume of 0.284 mL. By visual inspection a good adherence of PVDF fiber coating to the balloon service was observed.

Figure 13A:
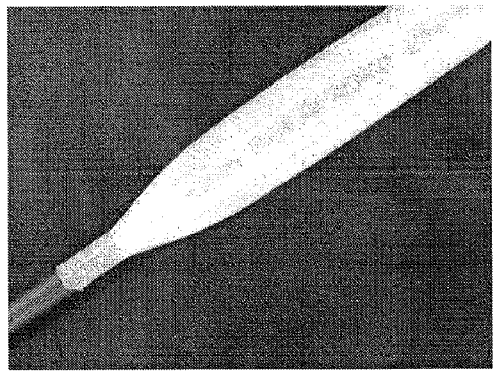
FIGS. 13a, 13b, 13c, and 13d are macroscopic and cross-section views of expandable members having fibrous coverings in accordance with another embodiment of the invention.
Figure 13B:
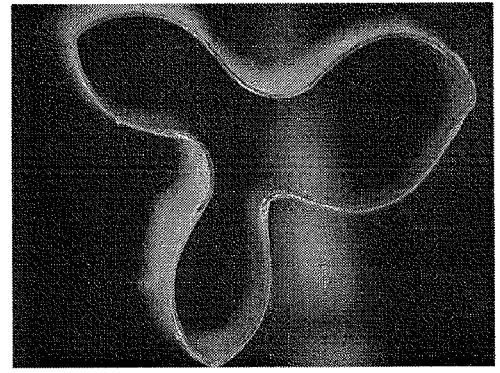
Figure 13C:
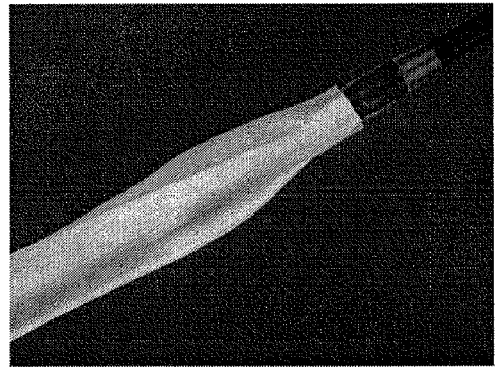
Figure 13D:
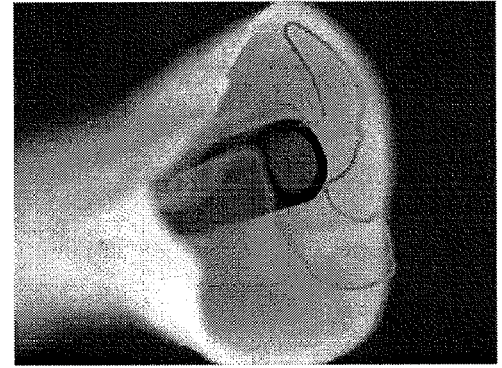

Example B 5 wt % of highly elastomeric poly(L-lactide-co-caprolactone) 50-50 copolymer (PCL-PLLA 50-50) in acetone was electrospun onto an inflated Pellethane balloon at nozzle voltage of +10 kv, target voltage of =5 kV, distance of 4.0 cm, and infusion rate of 1 mL/h (See, FIGS. 13a and 13b). Using identical processing parameters with the exception of a different balloon material, PCL-PLLA 50-50 was electrospun onto a folded Pebax balloon (See, FIGS. 13c and 13d). Adherence appeared greater on the Pellethane balloon compared with the Pebax balloon when cross-sections were optically imaged.

Example C

Figure 14A:
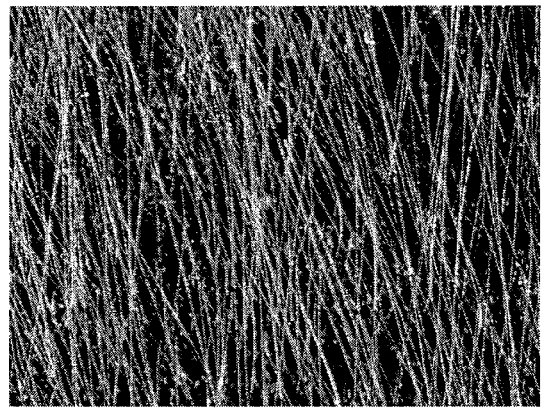
FIGS. 14a, 14b, and 14c are views of expandable members having fibrous coverings in accordance with another embodiment of the invention, with 14c including a stent engaged on the expandable member having a fibrous covering.
Figure 14B:
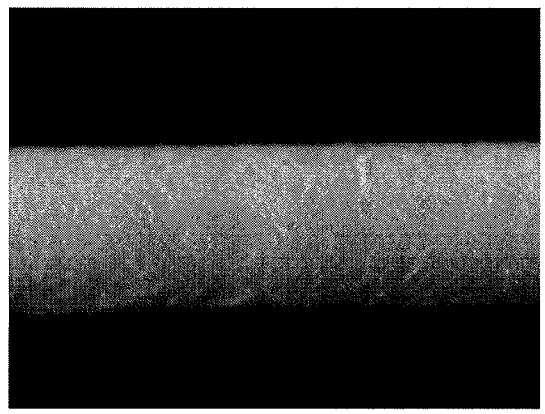
Figure 14C:
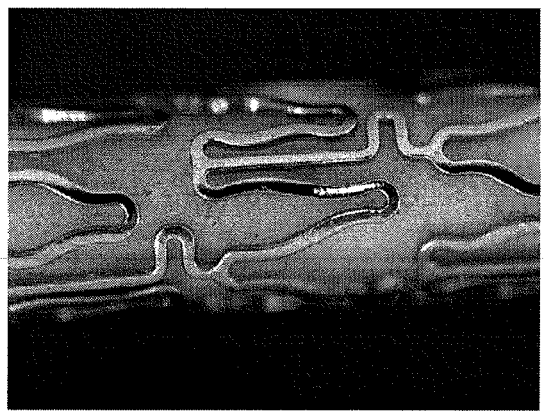

Under similar electrospinning conditions as described in Example A, PVDF was electrospun from acetone onto a 0.063" diameter stainless steel mandrel rotating and translating. The resulting fibrous conduit (Se, FIG. 14a and FIG. 14b) was removed from the mandrel and loaded onto a folded angioplasty balloon that was later crimped with a bare metal stent (See, FIG. 14c).

Figure 15A:
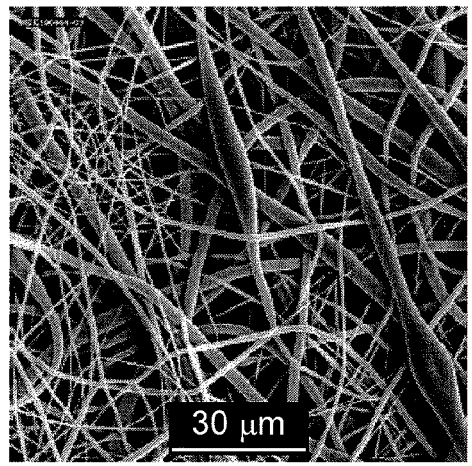
FIGS. 15a, 15b, 15c, and 15d are electron micrographs and optical images of fibrous coverings of the invention.
Figure 15B:
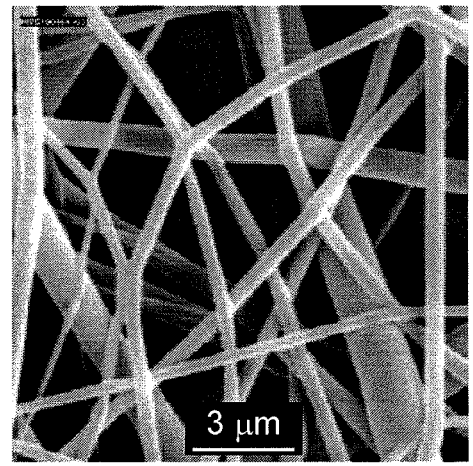
Figure 15C:
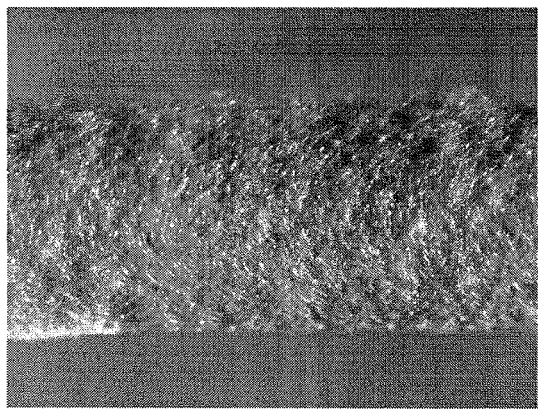
Figure 15D:
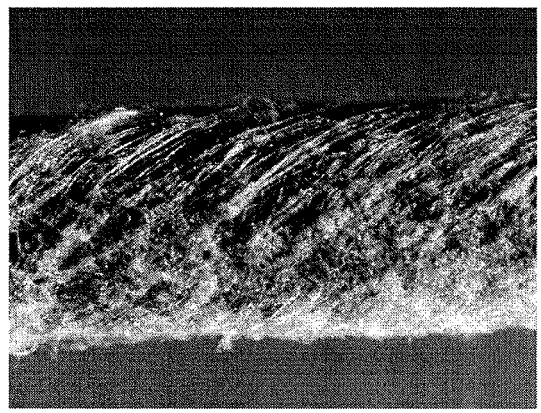
Figure 16A:
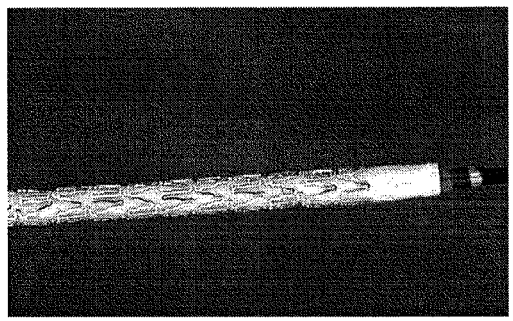
FIGS. 16a, 16b, 16c, 16d, 16e, 16f, 16g, and 16h are pre-inflation (16a-16d) and post-inflation (16e-16h) views of expandable members having fibrous coverings and stents engaged thereon in accordance with another embodiment of the invention.
Figure 16B:
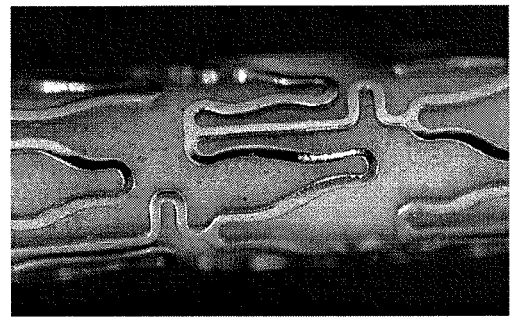
Figure 16C:
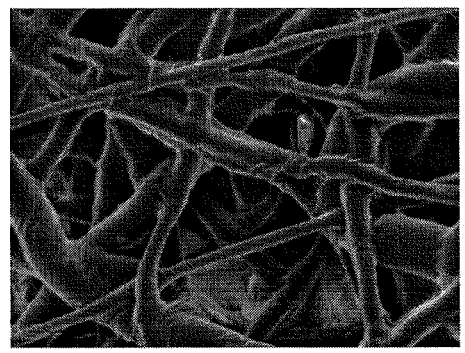
Figure 16D:
Figure 16E:
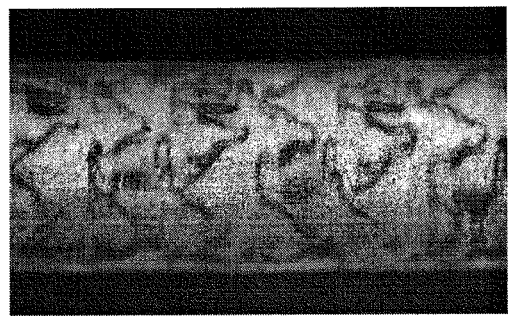
Figure 16F:
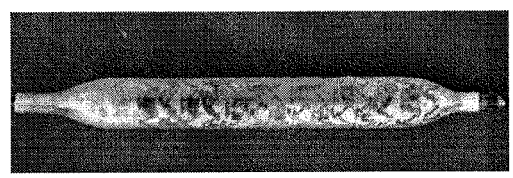
Figure 16G:
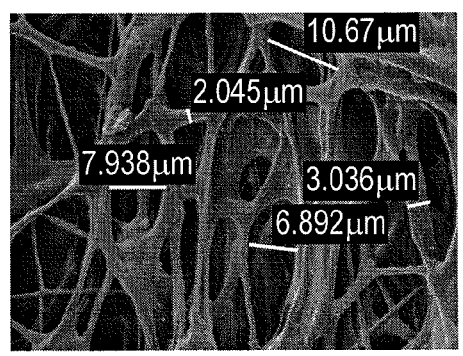
Figure 16H:
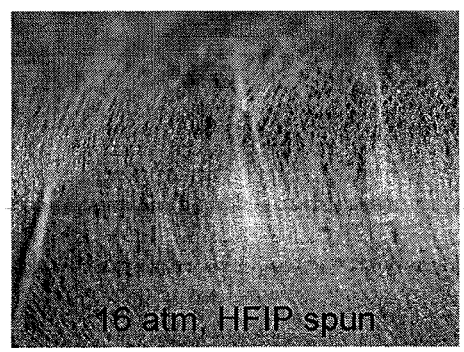

Example D 10 wt % Elasteon E2A silicone based polyurethane in tetrahydrofuran was electrospun onto a stainless steel mandrel. The resulting fibrous conduit was imaged by scanning electron microscopy (See FIGS. 15a and 15b) and an optical microscope (See FIGS. 15c and 15d) to illustrate the fibrous morphology.

Example E 10 wt % PCL-PLLA 50-50 in acetone was electrospun onto a stainless steel mandrel and then transferred onto a Vision angioplasty balloon later crimped with a bare metal stent (See, FIGS. 16a through 16d). Upon inflation to 16 atm, the stent was delivered and the pore size of the electrospun sock increased as imaged by microscopy (See FIGS. 16e through 16h). Upon deflation the material remained compressed on the balloon and helped maintain a low profile of 0.048"-0.050". Similarly as shown, PCL-PLLA 50-50 may also be processed from hexafluoroisopropanol solvent into a conduit and transferred onto the balloon.

Example F

A fibrous conduit was formed from 5 wt % of poly(L-lactide-co-ϵ-caprolactone) (PLCL) 50-50 in hexafluoroisopropanol solution by electrospinning. The PLCL had an inherent viscosity of 3.07 dl/g and a molecular weight of 561,000. Electrospinning equipment included a syringe pump (Harvard Apparatus PHD2200), a glove box, two power supply units (Gamma High Voltage Research), and a mandrel control stage that was designed and built in-house. Volumetric flow rate from the syringe pump was approximately 1 mL/hr and the PLCL solution was ejected through a stainless steel nozzle with a potential of approximately 12 kV. Electrospun fibers were directed toward an 0.053-inch diameter stainless steel mandrel spaced approximately 20 cm from the electrospinning nozzle and having a potential of approximately −6 kV. The mandrel was rotated by the mandrel control stage at 1500 RPM while the electrospinning nozzle was oscillated axially over 75 passes at an average linear speed of approximately 12 mm/s with a inflated Pellethane balloon at a nozzle voltage of +10 kv, target voltage of =5 kV, distance of 4.0 cm, and infusion rate of 1 mL/h (See, FIGS. 13a and 13b). Using identical processing parameters with the exception of a different balloon material, PCL-PLLA 50-50 was electrospun onto a folded Pebax balloon (See, FIGS. 13c and 13d). Adherence appeared greater on the Pellethane balloon compared with the Pebax balloon when cross-sections were optically imaged. The resulting fibrous conduit was removed from the mandrel for loading on a catheter device.

What is claimed is:

1. An intraluminal catheter device comprising:
    an elongated catheter shaft having a proximal end portion and a distal end portion, the shaft having an inflation lumen disposed between the proximal end portion and the distal end portion;
    an expandable member having an outer surface and an inner surface disposed proximate to the distal end portion of the catheter shaft, the expandable member having a coating of at least one therapeutic agent disposed on at least a portion of the outer surface; and
    a covering having a proximal end portion and a distal end portion, the covering positioned over at least a portion of the therapeutic agent coating on the outer surface of the expandable member, the covering formed of a matrix of fiber elements and attached to the catheter device by an attachment consisting of a bond at one of either the proximal end portion to a portion of the expandable member that is generally cylindrical after expansion of the expandable member or the distal end portion of the covering to a portion of the expandable member that is generally cylindrical after expansion of the expandable member.

2. The device of claim 1, wherein the matrix of fiber elements of the covering is formed of electrospun fiber elements.

3. The device of claim 1, wherein the fiber elements comprise a polymer selected from the group consisting of polyamides, polyurethanes, fluoropolymers, polyolefins, polyimides, polyimines, (methyl)acrylic polymers, polyesters, and co-polymers thereof.

4. The device of claim 1, wherein the attachment consists of the bond at the proximal end portion of the covering.

5. The device of claim 1, wherein the attachment consists of a bond at the distal end portion of the covering.

6. The device of claim 1, wherein the bond attaches the covering to the catheter shaft.

7. The device of claim 1, wherein the bond is selected from the group consisting of adhesion, thermal welding, heat shrink bands and direct solvent bonding.

8. The device of claim 1, wherein at least one of the proximal or distal end portions of the covering has a tapered end.

9. The device of claim 1, wherein the covering is essentially free of the at least one therapeutic agent.

10. The device of claim 1, wherein the matrix of fibers of the covering is relatively tightly woven to prevent the at least one therapeutic agent from entering between the fibers.

11. The device of claim 1, wherein the outer surface of the expandable member is textured to include a plurality of voids.

12. The device of claim 11, wherein the size of the voids ranges from 1 nanometer to 1 micron.

13. The device of claim 11, wherein the therapeutic agent of the therapeutic agent coating is loaded within the plurality of voids.

14. The device of claim 1, wherein the at least one therapeutic agent is selected from the group consisting of anti-proliferative, anti-inflammatory, antineoplastic, antiplatelet, anti-coagulant, anti-fibrin, antithrombonic, antimitotic, antibiotic, antiallergic and antioxidant compounds and combinations thereof.

15. The device of claim 1, wherein the expandable member is expandable from a first profile to a second profile.

16. The device of claim 1, wherein the matrix of fiber elements defines a plurality of gaps between the fibers.

17. The device of claim 1, wherein the covering formed of a matrix of fiber elements is separately formed and is slipped over the therapeutic agent coating on the outer surface of the expandable member.

18. The device of claim 1, wherein the covering formed of a matrix of fiber elements is formed directly over the therapeutic agent coating on the outer surface of the expandable member.

* * * * *